United States Patent
Beer et al.

(10) Patent No.: US 9,539,199 B2
(45) Date of Patent: Jan. 10, 2017

(54) COSMETIC COMPOSITIONS

(75) Inventors: Gerhard Beer, Burghausen (DE); Claudius Schwarzwaelder, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/235,289

(22) PCT Filed: Jul. 24, 2012

(86) PCT No.: PCT/EP2012/064461
§ 371 (c)(1),
(2), (4) Date: Jan. 27, 2014

(87) PCT Pub. No.: WO2013/014140
PCT Pub. Date: Jan. 31, 2013

(65) Prior Publication Data
US 2014/0161756 A1    Jun. 12, 2014

(30) Foreign Application Priority Data
Jul. 27, 2011    (DE) .......................... 10 2011 079 911

(51) Int. Cl.
A61Q 5/02         (2006.01)
A61Q 5/06         (2006.01)
A61Q 5/12         (2006.01)
A61K 8/898        (2006.01)
A61Q 5/00         (2006.01)
A61K 8/04         (2006.01)

(52) U.S. Cl.
CPC .............. A61K 8/898 (2013.01); A61K 8/046 (2013.01); A61Q 5/00 (2013.01); A61Q 5/006 (2013.01); A61Q 5/02 (2013.01); A61Q 5/12 (2013.01)

(58) Field of Classification Search
None
See application file for complete search history.

(56) References Cited

U.S. PATENT DOCUMENTS

| | | | |
|---|---|---|---|
| 6,090,885 A * | 7/2000 | Kuo et al. ...................... | 524/838 |
| 7,220,408 B2 | 5/2007 | Decoster et al. | |
| 7,223,385 B2 | 5/2007 | Gawtrey et al. | |
| 7,485,289 B2 | 2/2009 | Gawtrey et al. | |
| 7,504,094 B2 | 3/2009 | Decoster et al. | |
| 2008/0064813 A1 | 3/2008 | Schneider | |
| 2008/0107814 A1 | 5/2008 | Wierer et al. | |

FOREIGN PATENT DOCUMENTS

| | | |
|---|---|---|
| DE | 19826081 A1 | 12/1999 |
| DE | 102010020192 A1 | 11/2011 |
| EP | 0992528 A2 | 4/2000 |
| EP | 1921203 A1 | 5/2008 |
| WO | 2006119916 A1 | 11/2006 |

OTHER PUBLICATIONS

Kamath et al., "Measurement of combing forces", J. Soc. Cosmet. Chem., vol. 37, pp. 111-124 (1986).
Krummel et al, "The Chemistry and Manufacture of Cosmetics", vol. 11, pp. 359-396 (2000).
Lodge et al., "Wetting Properties of Human Hair by Means of Dynamic Contact Angle Measurement", , Journal of Applied Polymer Science, vol. 102, pp. 5255-5265 (2006).
International Cosmetic Ingredient Dictionary & Handbook, 13th Edition, The Personal Care Council (formerly: The Cosmetic, Toiletry, and Fragrance Association (CTFA)), 2010.
PatBase Abstract for DE 198 26 081.
PatBase Abstract for DE 10 2010 020 192.
International Search Report for PCT/EP2012/064461 dated Nov. 8, 2013.
M.D. Berthiaume, Society of Cosmetic Chemists (Publisher), Monograph, Silicones in Hair Care, pp. 1-88 (1997).
K. Schrader, A. Domsch, Cosmetology—Theory and Practice, vol. II, Verlag for chemische Industrie, pp. 11-8 to 11-22 (2005).

* cited by examiner

*Primary Examiner* — Jyothsna Venkat
(74) *Attorney, Agent, or Firm* — Caesar Rivise, PC

(57) ABSTRACT

The invention relates to a novel cosmetic composition, containing, in a cosmetically acceptable medium, at least one hair conditioning agent and at least one aqueous dispersion of pre-cross-linked organopolysiloxanes composed of units of general formula (I), wherein R means a monovalent, saturated or unsaturated hydrocarbon group having 1 to 200 carbon atoms per group, which hydrocarbon group can contain one or more heteroatoms from the group N, P, S, O, and halogen, $R^1$ means a hydrogen atom or an alkyl group having 1 to 8 carbon atoms per group, $R^2$ means a monovalent, optionally substituted hydrocarbon group having 1 to 18 carbon atoms per group, AKT is a group of the formula —$CH_2NHR^4$, —$CH2NR^4{}_2$, or formula (II), wherein $R^4$ means a monovalent hydrocarbon group having 1 to 18 carbon atoms, which hydrocarbon group can contain one or more heteroatoms from the group N and O, and $R^5$ means a divalent hydrocarbon group having 3 to 12 carbon atoms, which hydrocarbon group can contain one or more heteroatoms from the group N and O, b is 0.1 or 2, c is 0.1, 2, or 3, d is 0.1 or 2, and n is 0.1 or 2, with the stipulation that the sum n+b+c+d is ≤3, that at least one AKT group is contained per molecule on average, and that the organopolysiloxanes preferably form elastomeric films after the water is removed.

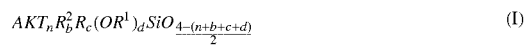

(I)

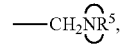

(II)

11 Claims, No Drawings

COSMETIC COMPOSITIONS

BACKGROUND OF THE INVENTION

The invention relates to cosmetic compositions comprising—in a cosmetically acceptable medium—at least one conditioning agent and at least one organopolysiloxane. Furthermore, the invention relates to a process for preparing the cosmetic compositions. Furthermore, the invention relates to the use of the cosmetic composition.

Organopolysiloxanes are used in cosmetic compositions, for example in haircare products, on account of their conditioning properties such as improving softness and smoothness, reducing combing forces, shine properties, improving color impressions, color protection properties, reducing electrostatic charging, protective properties during thermal stressing of the hair or hydrophobicization.

An overview of selected organopolysiloxanes for the care of keratin material such as hair can be found in M. D. Berthiaume, Society of Cosmetic Chemists (ed.), Monograph, Silicones in Hair Care, 1997 and J. Sejpka, Silicone in Haarpflegeprodukten [Silicones in haircare products], in: SÖFW-Journal, Volume 118, No. 17, 1992, pp. 1065-1070.

In everyday life, hair is exposed to a multitude of external influences which lead to damage of the hair surface, and as a result the cosmetic properties such as smoothness, softness, shine and other parameters deteriorate compared to undamaged hair. Damage to the hair surface can be caused for example by chemical or mechanical treatment, by UV radiation or by heat. Associated with the surface damage of hair is the destruction and partial removal of the lipid layer covering the cuticle, which is the reason for the highly hydrophobic property of undamaged, natural hair (R. A. Lodge, B. Bhusan, Wetting Properties of Human Hair by Means of Dynamic Contact Angle Measurement, Journal of Applied Polymer Science, Vol. 102, 5255-5265, 2006, Wiley). Compared to undamaged hair, damaged hair is considerably more hydrophilic since following destruction of the superficial lipid layer, a hydrophilic, amino-acid-based protein matrix acts as the hair surface.

U.S. Pat. No. 7,223,385 B2, U.S. Pat. No. 7,485,289 B2, U.S. Pat. No. 7,220,408 B2 and U.S. Pat. No. 7,504,094 B2 describe cosmetic compositions for treating hair which comprise special aminosilicones of the structure (I) or (II), as well as a conditioning agent or a thickener. The aminosilicones of the structure (I) or (II) are dimethylpolysiloxanes having terminal alkoxy/hydroxy groups with aminoethylaminopropyl-alkoxysiloxane units or aminoethylaminopropyl-methylsiloxane units, which are uncrosslinked.

According to US 2008/0064813 A1, aqueous dispersions of precrosslinked organopolysiloxanes are obtained without co-use of metal-containing catalysts by reacting organopolysiloxanes having alkoxy or hydroxy groups with reactive alkoxysilanes which have a group that increases the reactivity of the alkoxy group, such as a methyleneamino group. After applying the dispersions to substrates and evaporating the water, elastomeric films are obtained.

DESCRIPTION OF THE INVENTION

It is an object of the invention to achieve an improvement in cosmetic parameters for damaged hair, such as softness, smoothness, combing forces, shine and color properties, reduction in electrostatic charging and protective properties during thermal stress. In particular, the object consisted in increasing the hydrophobicity of the hair surface.

The invention provides a cosmetic composition comprising, in a cosmetically acceptable medium, at least one hair conditioning agent and at least one aqueous dispersion of precrosslinked organopolysiloxanes of units of the general formula $$AKT_n R^2_b R_c (OR^1)_d SiO_{\frac{4-(n+b+c+d)}{2}} \quad (I)$$

where
R may be identical or different and is a monovalent, saturated or unsaturated hydrocarbon radical having 1 to 200 carbon atoms per radical, which can contain one or more heteroatoms from the group N, P, S, O, and halogen,
$R^1$ may be identical or different and is a hydrogen atom or an alkyl radical having 1 to 18 carbon atoms (or 1 to 8 carbon atoms), can be interrupted by one or more separate oxygen atoms,
$R^2$ may be identical or different and is a monovalent, optionally substituted hydrocarbon radical having 1 to 18 carbon atoms per radical,
AKT is a radical of the formula —$CH_2NHR^4$, —$CH_2NR^4_2$ or

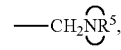

where
$R^4$ is a monovalent hydrocarbon radical having 1 to 8 carbon atoms, which can contain one or more heteroatoms from the group N and O, and
$R^5$ is a divalent hydrocarbon radical having 3 to 12 carbon atoms, which can contain one or more heteroatoms from the group N and O,
b is 0, 1 or 2,
c is 0, 1, 2 or 3,
d is 0, 1 or 2, and
n is 0, 1 or 2,
with the proviso that the sum n+b+c+d is ≤3 and that on average at least one radical AKT is present per molecule, and that the organopolysiloxanes preferably form elastomeric films after removing the water.

Aqueous dispersions of precrosslinked organopolysiloxanes and their preparation are described in US 2008/0064813 A1.

The aqueous dispersion of precrosslinked organopolysiloxanes is preferably obtained by reacting at least one organopolysiloxane (1) of units of the general formula $$R_c(OR^1)_d SiO_{\frac{4-(c+d)}{2}} \quad (II)$$

where R and $R^1$ have the meaning given for them above,
c is 0, 1, 2 or 3 and d is 0, 1 or 2,
with the proviso that the sum c+d is ≤3 and
in the organopolysiloxane (1) on average at least one radical $OR^1$ is present per molecule, preferably in the meaning of $R^1$ is hydrogen atom,
with at least one highly reactive silane (2) of the general formula $(AKT)_a R^2_b Si(OR^3)_{4-(a+b)}$ (III) or part hydrolyzates thereof where AKT and $R^2$ have the meaning given for them above,
$R^3$ is an alkyl radical having 1 to 8 carbon atoms per radical,
a is 1 or 2, preferably 1, and b is 0, 1 or 2, preferably 0 or 1,
with the proviso that the sum a+b is ≤3,
in the presence of water (3),
and emulsifier (4),
with the proviso that no metal-containing catalysts are co-used, and
that organopolysiloxane (1) and silane (2) are selected in type and amount such that the organopolysiloxanes are precrosslinked in the resulting dispersions.

In the preparation of the dispersions according to the invention, further substances which do not directly participate in the reaction can optionally be used.

The dispersions according to the invention therefore preferably comprise precrosslinked organopolysiloxanes consisting of units of the formula (I)
water (3)
emulsifier (4)

The dispersions according to the invention therefore preferably comprise no catalysts.

In the preparation of the dispersions according to the invention, organopolysiloxane (1) and silane (2) are selected in type and amount such that the organopolysiloxanes are precrosslinked in the resulting dispersions.

The dispersions according to the invention therefore already comprise precrosslinked organopolysiloxanes which, after removing the water, further crosslink and preferably form elastomeric films, which are preferably insoluble in toluene, where the crosslinked organopolysiloxanes have high molecular weight branched or dendrimer-like highly branched structures.

Here, "insoluble in toluene" is defined as follows: The elastomeric material that remains after evaporating the emulsion over a period of 48 h at 25° C. is defined as being insoluble in toluene if 3 g of the elastomeric material obtained by evaporation are insoluble in 7 g of toluene.

This is in contrast to uncrosslinked organopolysiloxanes, which may also be high-viscosity, but which are soluble in toluene.

Preferably, the dispersions according to the invention are aqueous suspensions or aqueous emulsions of precrosslinked organopolysiloxanes.

Upon drying—without the addition of catalyst or changing the pH—the dispersions according to the invention form a silicone network, preferably an elastic silicone network.

In the preparation of the precrosslinked organopolysiloxanes according to the invention, polyorganosiloxanes containing terminal OH groups and rapidly reacting crosslinkers are preferably required, and these components react with one another preferably at room temperature. To assist this reaction, no metal-containing, additional catalysts are required, i.e. preferably no transition metals of the VIII sub-group of the periodic table of the elements and compounds thereof and no metals of the III, IV and V main group of the periodic table of the elements and compounds thereof are used, with the elements C, Si, N, and P not being deemed metals in this definition.

The reaction also proceeds preferably in the neutral range, i.e. in the pH range from ca. 5 to 8, which arises by virtue of the components themselves. As a result of the high reactivity, a target-led chemical reaction is not necessary, nor preferably is heating.

Preferably, R is a monovalent, saturated or unsaturated hydrocarbon radical having 1 to 18 carbon atoms which can optionally contain one or more heteroatoms from the group N, P, S, O, and halogen.

Examples of hydrocarbon radicals R are alkyl radicals, such as the methyl, ethyl, n-propyl, isopropyl, 1-n-butyl, 2-n-butyl, isobutyl, tert-butyl, n-pentyl, isopentyl, neopentyl, tert-pentyl radical; hexyl radicals, such as the n-hexyl radical; hepty radicals, such as the n-heptyl radical; octyl radicals, such as the n-octyl radical and isooctyl radicals, such as the 2,2,4-trimethylpentyl radical; nonyl radicals, such as the n-nonyl radical; decyl radicals, such as the n-decyl radical; dodecyl radicals, such as the n-dodecyl radical; octadecyl radicals, such as the n-octadecyl radical; cycloalkyl radicals, such as the cyclopentyl, cyclohexyl, cycloheptyl radical and methylcyclohexyl radicals; alkenyl radicals, such as the vinyl, 5-hexenyl, cyclohexenyl, 1-propenyl, allyl, 3-butenyl and 4-pentenyl radical; aryl radicals, such as the phenyl, naphthyl, anthryl and phenanthryl radical; alkaryl radicals, such as o-, m-, p-tolyl radicals; xylyl radicals and ethylphenyl radicals; and aralkyl radicals, such as the benzyl radical, the α- and the β-phenylethyl radical.

As radical R, preference is given to the methyl, ethyl, octyl and phenyl radical, and particular preference is given to the methyl and ethyl radical.

Examples of substituted radicals R are haloalkyl radicals, such as the 3,3,3-trifluoro-n-propyl radical, the 2,2,2,2',2', 2'-hexafluoroisopropyl radical, the heptafluoroisopropyl radical and haloaryl radicals, such as the o-, m- and p-chlorophenyl radical.

Further examples of substituted radicals R are all of the radicals mentioned above for R which can contain one or more N atoms. Preferred examples of substituted radicals R are therefore amino radicals A of the general formula

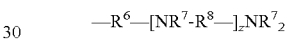

where $R^6$ is a divalent linear or branched hydrocarbon radical having 3 to 18 carbon atoms, preferably an alkylene radical having 3 to 10 carbon atoms,
$R^2$ is a hydrogen atom, an alkyl radical having 1 to 8 carbon atoms or an acyl radical, such as acetyl radical, preferably a hydrogen atom,
$R^8$ is a divalent hydrocarbon radical having 1 to 6 carbon atoms, preferably an alkylene radical having 1 to 6 carbon atoms,
z is 0, 1, 2, 3 or 4, preferably 0 or 1.

A further example of substituted radicals R are polyether radicals E of the general formula

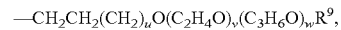

where
$R^9$ is a hydrocarbon radical having 1 to 6 carbon atoms,
u is 0 or an integer from 1 to 16, preferably 1 to 4,
v is 0 or an integer from 1 to 35, preferably 1 to 25, and
w is 0 or an integer from 1 to 35, preferably 1 to 25,
with the proviso that the sum v+w is 1 to 70, preferably 1 to 50.

Examples of radical $R^1$ are the alkyl radicals listed above for R, and also the methoxyethyl radical, the ethoxyethyl radical and hexoxyethyl radical, with the radical $R^1$ preferably being hydrogen and the methyl radical and the ethyl radical.

Examples of hydrocarbon radicals R apply in their entirety to radicals $R^2$.

Preferred examples of radicals $R^3$ are the methyl radical and ethyl radical, particularly preferably the ethyl radical.

Examples of hydrocarbon radicals R, such as alkyl, cycloalkyl, aryl, alkaryl and aralkyl radicals R, apply in their entirety to hydrocarbon radicals $R^4$, with preference being given to the radicals of the formula

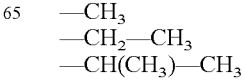

—$CH_2$—$CH_2$—$CH_2$—$CH_3$
—$CH_2$—$CH(CH_3)$—$CH_3$
cyclohexyl and
phenyl.

Examples of hydrocarbon radicals $R^4$ which contain N and/or O atoms are
—$(CH_2)_2N(CH_3)_2$
—$(CH_2)_3N(CH_3)_2$
phenyl-$NH_2$
phenyl-$OCH_3$ Examples of divalent hydrocarbon radicals $R^5$ are alkylene radicals having 3 to 12 carbon atoms.

Examples of hydrocarbon radicals $R^5$ which contain N and/or O atoms are radicals of the formula
—$CH_2$—$CH_2$—O—$CH_2$—$CH_2$—
—$CH_2$—$CH_2$—NH—$CH_2$—$CH_2$— and
—$CH_2$—$CH_2$—NH—$CH_2$—.

A preferred example of $R^5$ is the radical of the formula
—$CH_2$—$CH_2$—O—$CH_2$—$CH_2$—.

Examples of hydrocarbon radicals $R^9$ are alkylradicals, such as the methyl, ethyl, n-propyl, isopropyl, 1-n-butyl, 2-n-butyl, isobutyl, tert-butyl, n-pentyl, isopentyl, neopentyl, tert-pentyl radical, hexyl radicals, such as the n-hexyl and the isohexyl radical.

A preferred radical $R^9$ is a methyl radical.

In the preparation of the dispersions according to the invention, the organopolysiloxanes (1) used are preferably siloxanes of the general formula $$(R^1O)R_2SiO(SiR_2O)_eSiR_2(OR^1) \tag{IVa}$$

where R and $R^1$ have the meaning given for them above and e is an integer from 1 to 1000.

In the preparation of the dispersions according to the invention, the organopolysiloxanes (1) used are preferably siloxanes of the general formula $$(R^1O)R'_2SiO(SiR'_2O)_eSiR'_2(OR^1) \tag{IVb}$$

where $R^1$ and e have the meaning given for them above and R' can be identical or different and is a monovalent hydrocarbon radical having 1 to 18 carbon atoms, with the proviso that 25 to 100%, preferably 50 to 100%, of all of the radicals $R^1$ are hydrogen atoms.

In the preparation of the dispersions according to the invention, the organopolysiloxanes (1) used are particularly preferably amine oils, i.e. siloxanes of the general formula $$(R^1O)R'_2SiO(SiAR'O)_p(SiR'_2O)_qSiR'_2(OR^1) \tag{IVc}$$

where R' and $R^1$ have the meaning given for them above, the amino radical A has the meaning given for it above, p is an integer from 1 to 1000, preferably 1 to 10 and q is 0 or an integer from 1 to 2000, preferably 50 to 1000, with the proviso that 10 to 100%, preferably 20 to 100%, of all of the radicals $R^1$ are hydrogen atoms.

Within the context of this invention, formula (IVc) should be understood as meaning that p units —(SiAR'O)— and q units —(SiR'$_2$O)— can be distributed in any desired manner, for example blockwise or randomly, within the organopolysiloxane molecule.

Preference is therefore given to aqueous dispersions of precrosslinked organopolysiloxanes of units of the general formula $$AKT_nR_b^2A_mR'_c(OR^1)_dSiO_{\frac{4-(n+m+b+c+d)}{2}} \tag{I'}$$

where AKT, A, R', $R^1$, $R^2$, b, c, d and n have the meaning given for them above,
m is 0 or 1, with the proviso that the sum n+m+b+c+d is ≤3 and n and m in the same siloxane unit are not simultaneously 1 and that on average at least one radical AKT and a radical A is present per molecule.

Examples of hydrocarbon radicals R apply in their entirety to hydrocarbon radicals R'.

Examples of radicals A are:
—$(CH_2)_3NH_2$
—$(CH_2)_3$—NH—$(CH_2)_2$—$NH_2$
—$CH_2CH(CH_3)$ $CH_2$—NH— $(CH_2)_2$—$NH_2$
—$(CH_2)_3$—NH (cyclohexyl)
—$(CH_2)_3$—$NHCH_3$
—$(CH_2)_3$—$N(CH_3)_2$
—$(CH_2)_3$—$NHCH_2CH_3$
—$(CH_2)_3$—$N(CH_2CH_3)_2$
—$(CH_2)_4$—$NH_2$
—$CH_2CH(CH_3)$ $CH_2$—$NH_2$
—$(CH_2)_3$—NH—$(CH_2)_2$—$NHCH_3$
—$(CH_2)_3$—NH—$(CH_2)_2$—$N(CH_3)_2$
—$(CH_2)_3$—NH—$(CH_2)_2$—$NHCH_2CH_3$
—$(CH_2)_3$—NH—$(CH_2)_2$—$N(CH_2CH_3)_2$
—$(CH_2)_3[$—NH—$CH_2CH_2]_2$—$NH_2$ and their partially or completely acetylated forms, such as
—$(CH_2)_3$—NH(acetyl)
—$(CH_2)_3$—NH— $(CH_2)_2$—NH (acetyl) and
—$(CH_2)_3$—N(acetyl)-$(CH_2)_2$—NH(acetyl).

Preferred examples of radicals A are:
—$(CH_2)_3NH_2$
—$(CH_2)_3$—NH— $(CH_2)_2$—$NH_2$
—$CH_2CH(CH_3)$ $CH_2$—NH— $(CH_2)_2$—$NH_2$
—$(CH_2)$ 3-$NHCH_3$
—$(CH_2)_3$—NH (cyclohexyl)
—$(CH_2)_3$—NH(acetyl)
—$(CH_2)_3$—NH— $(CH_2)_2$—NH (acetyl) and
—$(CH_2)_3$—N(acetyl)-$(CH_2)_2$—NH(acetyl).

In the preparation of dispersions according to the invention, the organopolysiloxanes (1) used can also be those siloxanes (resins) of the general formula $$[(R_3SiO_{1/2})_f(R_2SiO_{2/2})_g(RSiO_{3/2})_h(SiO_{4/2})_k] \tag{V}$$

where R has the meaning given for it above and additionally R in formula (V) can also be equal to $(OR^1)$ with the meaning given for it above, with the proviso that at least one radical —$OR^1$, where $R^1$ is a hydrogen atom, is present per molecule.
f, g, h and k is an integer from 0 to 1000 and h/(f+g+h+k) is preferably >0.2.

Examples of siloxanes (1) are standard commercial polydimethylsiloxanes with terminal silanol groups and polydimethylsiloxanes with terminal alkoxy and silanol groups.

Further examples of siloxanes (1) are standard commercial functionalized siloxanes, such as amine oils, e.g. amine oils with 3-(2-aminoethyl)aminopropyl functions, glycol oils, phenyl or phenylmethyl oils which contain silanol groups or alkoxy and silanol groups.

Further examples of siloxanes (1) are resin-like siloxanes, e.g. methylsilicone resins, with 80 mol % $CH_3SiO_{3/2}$ and 20 mol % $(CH_3)_2SiO_{2/2}$ and a molar mass of ca. 5000 g/mol or 98 mol % $CH_3SiO_{3/2}$ and 2 mol % $(CH_3)_2SiO_{2/2}$ and a molar mass of ca. 5000 g/mol, or e.g. methylphenylsilicone resins with 65 mol % $C_6H_5SiO_{3/2}$ and 35 mol % $(CH_3)_2SiO_{2/2}$, the residual free valences of which carry $R^1O$ groups with the aforementioned meaning.

In the preparation of the dispersions according to the invention, one type of organopolysiloxane (1) can be used or different types of organopolysiloxane (1) can be used.

The organopolysiloxanes (1) used in the preparation of the dispersions according to the invention preferably have viscosities from 1 mPa·s to 50 000 000 mPa·s at 25° C., preferably 50 mPa·s to 10 000 000 mPa·s at 25° C. and particularly preferably 100 mPa·s to 500 000 mPa·s at 25° C.

In the preparation of the dispersions according to the invention, one type of silane (2) can be used or different types of silane (2) can be used.

Examples of radicals AKT are the aminomethyl, methylamino-methyl, dimethylaminomethyl, diethylaminomethyl, dibutylaminomethyl, cyclohexylaminomethyl, morpholinomethyl, piperidinomethyl and piperazinomethyl radical, preference being given to the cyclohexylaminomethyl and morpholinomethyl radical.

Examples of silanes (2) are diethylaminomethylmethyldimethoxysilane, dibutylaminomethyltriethoxysilane, dibutylaminomethyltributoxysilane, cyclohexylaminomethyltrimethoxysilane, cyclohexylaminomethyltriethoxysilane, cyclohexylaminomethylmethyldiethoxysilane, anilinomethyltriethoxysilane, anilinomethylmethyldiethoxysilane, morpholinomethyltriethoxysilane, morpholinomethyltrimethoxysilane, morpholinomethyltriisopropoxysilane, 3-dimethylaminopropylaminomethyltrimethoxysilane, morpholinomethyltributoxysilane, morpholinomethyltrialkoxysilane, where the alkoxy radical is a $C_1$-$C_4$-alkoxy radical, in particular a mixture of methoxy radical and ethoxy radical, piperazinomethyltriethoxysilane and piperidinomethyltriethoxysilane.

Preference is given here to silanes (2) which carry a trialkoxy group, i.e. in which b in formula (III) is 0.

The precrosslinked organopolysiloxanes can have, depending on the use of di- or trialkoxysilane (2) or partial hydrolyzate, carrying alkoxy and hydroxy groups, of (2) and linear, branched or resin-like siloxane (1), branched or even highly branched/highly crosslinked structures with linear fractions.

If dialkoxysilanes (2) with purely linearly structured siloxanes (1) which contain at most 2 SiOH functions per molecule, in particular with the siloxanes of the formulae (IVa) or (IVb), are reacted, linear high-viscosity organopolysiloxanes, and not crosslinked organopolysiloxanes according to the invention are obtained. The reaction of siloxanes (1) which contain more than 2 OH functions, in particular at least 3 OH functions, per molecule, with dialkoxysilanes (2), by contrast, leads to crosslinked siloxane polymers.

If the silanes (2) used are trialkoxysilanes, which is preferred, precrosslinked organopolysiloxanes according to the invention are obtained. Furthermore, also when using mixtures of dialkoxysilanes (2) and trialkoxysilanes (2), particularly when using mixtures of 1-99% by weight dialkoxysilanes (2) and 1-99% by weight trialkoxysilanes (2), preferably 10-90% by weight dialkoxysilanes (2) and 10-90% by weight trialkoxysilanes (2), precrosslinked organopolysiloxanes according to the invention are obtained.

The degree of crosslinking here depends on the ratio of the equivalents —$OR^3$ in silane (2) to —$OR^1$ in siloxane (1) used.

To prepare the dispersions according to the invention of siloxane (1) and highly reactive silane (2), silane (2) or its partial hydrolyzates is used here preferably in amounts of from 0.6 to 5 equivalents of —$OR^3$, preferably 0.65 to 2 equivalents of —$OR^3$, particularly preferably 0.7 to 1.5 equivalents of —$OR^3$, per equivalent of —$OR^1$ in siloxane (1), where $R^1$ is preferably a hydrogen atom.

The preparation of the dispersions according to the invention of precrosslinked organopolysiloxanes takes place by intensive mixing of siloxanes from the group of the siloxanes (1) with silanes (2)
water (3), and
emulsifiers (4) with one another. The preparation can take place discontinuously or continuously.

Although, as is known, the silanes (2) contain hydrolysis-sensitive groups, particularly if $R^3$ is a methyl or ethyl, precrosslinked organopolysiloxanes are surprisingly obtained by reaction with siloxanes (1) even in the presence of water.

The nature of the mixing of the components which are used for the preparation of the dispersions according to the invention is not very critical and can be performed in various sequences. However, depending on the components (1), (2), (3) and (4), preferred procedures may arise, which should be tested on a case by case basis.

For example, the components (1) and (2) can be premixed with one another, then the emulsifier(s) added and then water (3) incorporated. It is also possible to meter in the components (1) to (4) into the emulsifying apparatus in order. In special cases, it may be advantageous, e.g. on account of the siloxane viscosity or reactivity, to mix silane (2) with a siloxane (1) and then to incorporate another siloxane (1), or vice versa, depending on how more favorable rheological properties for the processing of the components arise.

In the case of very reactive silanes (2), it may be advantageous to first convert the component (1) into a rigid phase with emulsifier (4) and water (3), and then to meter in the silane (2) in pure form or diluted in an inert substance, before a phase conversion and thus e.g. an oil-in-water dispersion, is obtained.

Furthermore, it is also possible to add silane (2) to the finished emulsion of siloxanes (1) in order, in so doing, to achieve the desired reaction and crosslinking of the siloxane (1) in the emulsion. Furthermore, the silane (2) can be partially or completely hydrolyzed beforehand by adding water. In order to obtain VOC-free hydrolyzate of (2), the by-product alcohol $R^3OH$ can be partially or completely removed by suitable known measures such as distillation, membrane processes or other separation processes.

In the preparation of the dispersions according to the invention, water (3) is used in amounts of preferably 1 to 99% by weight, particularly preferably 25 to 95% by weight, in each case based on the total weight of all of the ingredients in the dispersion.

The aqueous dispersion according to the invention of precrosslinked organopolysiloxanes is used as oil in water system.

Emulsifiers (4) which can be used for preparing the aqueous dispersions of precrosslinked organopolysiloxanes are all hitherto known anionic, nonionic, cationic or amphoteric emulsifiers, either individually or in the form of mixtures of different emulsifiers, with which also hitherto aqueous dispersions, in particular aqueous emulsions of organopoly-siloxanes, have been able to be prepared.

Examples of anionic emulsifiers are:
1. Alkyl sulfates, particularly those with a chain length from 8 to 18 carbon atoms, alkyl and alkaryl ether sulfates with 8 to 18 carbon atoms in the hydrophobic radical and 1 to 40 ethylene oxide (EO) or propylene oxide (PO) units.
2. Sulfonates, particularly alkylsulfonates with 8 to 18 carbon atoms, alkylarylsulfonates with 8 to 18 carbon atoms, taurides, esters and half-esters of sulfosuccinic acid with monohydric alcohols or alkylphenols with 4 to 15 carbon atoms; optionally, these alcohols or alkylphenols may also be ethoxylated with 1 to 40 EO units.

3. Alkali metal and ammonium salts of carboxylic acids with 8 to 20 carbon atoms in the alkyl, aryl, alkaryl or aralkyl radical.

4. Phosphoric acid partial esters and their alkali metal and ammonium salts, particularly alkyl and alkaryl phosphates with 8 to 20 carbon atoms in the organic radical, alkyl ether and alkaryl ether phosphates with 8 to 20 carbon atoms in the alkyl or alkaryl radical and 1 to 40 EO units.

Examples of nonionic emulsifiers are:

5. Polyvinyl alcohol which also has 5 to 50%, preferably 8 to 20%, vinyl acetate units, with a degree of polymerization of 500 to 3000.

6. Alkyl polyglycol ethers, preferably those with 3 to 40 EO units and alkyl radicals from 8 to 20 carbon atoms.

7. Alkylaryl polyglycol ethers, preferably those with 5 to 40 EO units and 8 to 20 carbon atoms in the alkyl and aryl radicals.

8. Ethylene oxide/propylene oxide (EO/PO) block copolymers, preferably those with 8 to 40 EO or PO units.

9. Addition products of alkylamines with alkyl radicals from 8 to 22 carbon atoms with ethylene oxide or propylene oxide.

10. Fatty acids with 6 to 24 carbon atoms.

11. Alkyl polyglycosides of the general formula R"—O—$Z_O$, in which R" is a linear or branched, saturated or unsaturated alkyl radical with on average 8-24 carbon atoms and $Z_O$ is an oligoglycoside radical with on average o=1-10 hexose or pentose units or mixtures thereof.

12. Natural substances and derivatives thereof, such as lecithin, lanolin, saponins, cellulose; cellulose alkyl ethers and carboxyalkyl celluloses, the alkyl groups of which in each case have up to 4 carbon atoms.

13. Linear organo(poly)siloxanes containing polar groups, containing in particular the elements O, N, C, S, P, Si, in particular those with alkoxy groups with up to 24 carbon atoms and/or up to 40 EO and/or PO groups.

Examples of cationic emulsifiers are:

14. Salts of primary, secondary and tertiary fatty amines with 8 to 24 carbon atoms with acetic acid, sulfuric acid, hydrochloric acid and phosphoric acids.

15. Quaternary alkyl- and alkylbenzeneammonium salts, in particular those whose alkyl groups have 6 to 24 carbon atoms, in particular the halides, sulfates, phosphates and acetates.

16. Alkylpyridinium, alkylimidazolinium and alkyloxazolinium salts, in particular those whose alkyl chain has up to 18 carbon atoms, specifically the halides, sulfates, phosphates and acetates.

Suitable amphoteric emulsifiers are in particular:

17. Long-chain substituted amino acids, such as N-alkyl-di (aminoethyl)glycine or N-alkyl-2-aminopropionic acid salts.

18. Betaines, such as N-(3-acylamidopropyl)-N,N-dimethylammonium salts with a $C_8$-$C_{18}$-acyl radical and alkylimidazolium betaines or quaternized alkyl or substituted alkyl derivatives of N,N-dimethylglycine.

Preferred emulsifiers for preparing aqueous dispersions of precrosslinked organopolysiloxanes are nonionic emulsifiers, in particular the alkyl polyglycol ethers listed above under 6.

Constituent (4) can consist of one of the aforementioned emulsifiers or of a mixture of two or more of the aforementioned emulsifiers, it can be used in pure form or as solutions of one or more emulsifiers in water or organic solvents.

In the preparation of the dispersions according to the invention, the emulsifiers (4) are used in amounts of preferably 0.1 to 60% by weight, particularly preferably 0.5 to 30% by weight, in each case based on the total weight of siloxanes (1) and silanes (2).

If the organopolysiloxane (1) or the silane (2) or the precrosslinked organopolysiloxane formed itself acts as emulsifier, it is possible to dispense with the addition of separate emulsifier (4).

The emulsifying operation for preparing the dispersion is carried out preferably at temperatures below 120° C., preferably at 5° C. to 100° C., particularly preferably at 10° C. to 80° C. The temperature increase is preferably brought about by introducing mechanical shear energy which is required for the emulsifying process. The temperature increase is not required for increasing the rate of a chemical process. Furthermore, the preparation of the dispersions preferably takes place at the pressure of the ambient atmosphere, although it can also be carried out at higher or lower pressures.

The reaction of (1) with (2) during the preparation of the dispersions proceeds to completion preferably within a few minutes to several hours, with methoxysilanes reacting more quickly than ethoxysilanes.

The alcohols produced during the preparation of the dispersions as condensation by-products can remain in the product or else be removed, for example by distillation in vacuo, membrane processes, or by extraction.

The average particle size measured by means of light scattering in the dispersions according to the invention is preferably in the range 0.001 to 50 µm, preferably at 0.005 to 10 µm, particularly preferably in the range 0.01 to 5 µm. The pH values can vary from 1 to 14, preferably 3 to 9, particularly preferably 4 to 8.

The cosmetic composition according to the invention comprises aqueous dispersions of precrosslinked organopolysiloxanes preferably in amounts of 0.2 to 40% by weight, preferably from 0.5 to 30% by weight, especially preferably 1 to 20% by weight, in each case based on the total weight of the cosmetic composition.

The cosmetically acceptable medium in the cosmetic composition according to the invention is preferably water.

The cosmetic composition according to the invention comprises at least one hair conditioning agent, hereinbelow simply called conditioner. Analogously to K. Krummel, Stephane Chiron, J. Jachowicz, Chapter 14, in: "The Chemistry and Manufacture of Cosmetics", Volume II, Formulating, Third Edition by Mitchell L. Schlossmann, 2000, pp. 359-396, conditioners is the term used to refer to cosmetic ingredients which modify the hair surface and influence the nature of the hair. Cosmetic compositions comprising conditioners are used for modifying or improving the softness of the hair, better detanglability, reduction in wet and dry combing force, care of the hair, avoidance of electrostatic charging, easier sliding effect through the hair and along the hair surface, improvement in hair shine, retention of color fastness of hair, reduction in hair breakage, retention of hair shape and further cosmetic properties which are associated with natural and healthy hair.

The cosmetic composition according to the invention improves one or more of the aforementioned effects.

Examples of conditioners and their INCI names are described in the "International Cosmetic Ingredient Dictionary & Handbook" from the Personal Care Product Council (ed.). As reference, it is possible to use the world wide web-based "wINCI Web Based International Cosmetic Ingredient Dictionary & Handbook (http://online.personal-carecouncil.org/jsp/Home.jsp) or the International Cosmetic Ingredient Dictionary & Handbook, 13th Edition, The Personal Care Products Council (formerly: The Cosmetic, Toiletry, and Fragrance Association (CTFA)), 2010.

Preferred examples of conditioners are cationic polymers. These are understood as meaning polymers which carry, in the pendant or terminal position, cationic groups or, in the pendant or terminal position, groups which can be converted to a cationic group by ionization.

Preference is given to using cationic polymers which have a quaternary ammonium group.

Examples of cationic polymers that can preferably be used are published in the International Cosmetic Ingredient Dictionary & Handbook under the name Polyquaternium, with each polymer being identified by an individual numerical abbreviation, e.g. Polyquaternium-1.

Further examples of cationic polymers are derivatives, having quaternary ammonium groups, of modified polysaccharides, e.g. polymers with the INCI names *Cassia* Hydroxypropyltrimonium Chloride, derivatives of modified cellulose and/or starch, e.g. a quaternary ammonium derivative of a *cyamopsis tetragonoloba* (guar) gum modified with propylene glycol ether and having the INCI name Guar Hydroxypropyltrimonium Chloride, or polymeric quaternary ammonium salts of the reaction product of hydroxyethylcellulose with a trimethylammonium-substituted epoxide, such as cellulose, 2-hydroxyethyl 2-(2-hydroxy-3-(trimethylammonium)propoxy)ethyl 2-hydroxy-3-(trimethylammonium)propyl ether chloride, such as cellulose, 2-hydroxyethyl 2-hydroxy-3-(trimethylammonium)propyl ether, chloride, such as cellulose, 2-hydroxyethyl 23-hydroxy-3-(trimethylammonium)propyl ether, chlorides, such as cellulose, 2-[2-hydroxy-3-(trimethylammonium)propoxy]ethyl ether, chlorides, with the INCI name Polyquaternium-10.

Further examples of cationic polymers are acrylic acid polymer derivatives, acrylic acid copolymer derivatives, methacrylic acid derivatives and methacrylic acid copolymer derivatives having quaternary ammonium groups, e.g. polymers with the INCI name Polyquaternium-37.

Further examples of cationic polymers are copolymers of dimethyldiallylammonium chlorides and acrylic acid that have quaternary ammonium groups, e.g. polymers with the INCI name Polyquaternium-22.

Further examples of cationic polymers are copolymers, having quaternary ammonium groups, of derivatives of vinylpyrrolidone, vinylimidazole and vinylimidazoline and methacrylic acid, e.g. polymers with the INCI name Polyquaternium-86.

Further examples of cationic polymers are copolymers, having quaternary ammonium groups, of acrylamides and dimethyldiallylammonium chlorides, e.g. polymers with the INCI name Polyquaternium-7.

Further examples of cationic polymers are copolymers, having quaternary ammonium groups, of the reaction product diethyl sulfate with vinylpyrrolidone and dimethylaminoethyl methacrylate, e.g. polymers with the INCI name Polyquaternium-11.

The cosmetic composition according to the invention comprises cationic polymers preferably in amounts of from 0.01 to 5% by weight, preferably from 0.05 to 4% by weight, particularly preferably 0.10 to 3% by weight, in each case based on the total weight of the cosmetic composition.

Further preferred examples of conditioners are cationic surfactants. Examples of preferably used cationic surfactants correspond to the materials listed in points 14 to 16 under examples of cationic emulsifiers. Examples are cetyltrimethylammonium salts or behenyltrimethylammonium salts. As anionic counterion, for example, chloride, bromide, methosulfate may be present. INCI names of preferably used cationic surfactants are, for example, cetrimonium chloride, cetrimonium methosulfate, behentrimonium chloride, behentrimonium methosulfate, steartrimonium bromide.

The cosmetic composition according to the invention comprises cationic surfactants preferably in amounts of from 0.1 to 7% by weight, preferably from 0.15 to 6% by weight, especially preferably 0.2 to 5% by weight, in each case based on the total weight of the cosmetic composition.

Further examples of conditioners are quaternary ammonium compounds present in nonpolymeric form. This is understood as meaning nonpolymeric ammonium compounds which are present in cationic form or can be converted into a cationic group by ionization.

Examples of preferably used quaternary ammonium compounds present in nonpolymeric form are dimethyl dioctadecyl ammonium chloride with the INCI name Distearyldimonium Chloride, N-[3-(dimethylamino)propyl] octadecanamide with the INCI name Stearamidopropyl Dimethylamine or compounds with the INCI name Dicocoylethyl Hydroxyethylmonium Methosulfate or Quaternium-87.

Further preferred examples of conditioners are organopolysiloxanes and organopolysiloxane copolymers which are different from the precrosslinked organopolysiloxanes of the formula (I) present in the aqueous dispersions. The organopolysiloxanes can be present in the form of an oil, wax, gum or resin or in the form of an emulsion.

Examples of such organopolysiloxanes different from organopolysiloxanes of the formula (I) are: cyclic organopolysiloxanes of the formula

$$[R^*_2SiO]_x$$

where x is an integer from 4 to 8,
linear organopolysiloxanes of the general formula

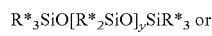
$$R^*_3SiO[R^*_2SiO]_ySiR^*_3 \text{ or}$$

$$HOSiR^*_2O[R^*_2SiO]_ySiR^*_2OH,$$

where y is 0 or an integer from 1 to 2000,
and resin-like organopolysiloxanes of the general formula

$$R^*_tSiO_{(4-t)/2}$$

where R* in each case has the meaning of R', A or E given for them above, and
t is 0, 1, 2 or 3,
such that the organopolysiloxane resin is composed of M, D, T and/or Q units, where the combination of predominantly or exclusively D and T units are likewise preferred, and the combination of predominantly or exclusively M and Q units, where in the case of the resins composed predominantly or exclusively of D and T units, T units are preferably present in a molar ratio of T/[M+D+T+Q] of 0.45 to 1, particularly preferably from 0.55 to 1.0, and the number of M and Q units in both cases is preferably zero, and in the case of the organopolysiloxane resins composed predominantly or exclusively of M and Q units, Q units are present preferably in a molar ratio of Q/[M+D+T+Q] of from 0.25 to 0.9, particularly preferably from 0.35 to 0.7, and the number of D and T units in both cases is preferably zero.

Examples of organopolysiloxanes, present in the form of an oil are polydimethylsiloxanes with a viscosity 0.65 to 2 000 000 mPas (25° C.) and the INCI names Disiloxane and Dimethicone.

Further examples of organopolysiloxanes, present in the form of an oil or wax, are functionalized organopolysiloxanes, for example polyalkylsiloxanes, where at least one alkyl radical differs from methyl, for example organopolysiloxanes with the INCI name Stearyl Dimethicone, Cetyl Dimethicone or C26-28 Alkyl Dimethicone,
or for example polyarylsiloxanes and polyarylalkylsiloxanes, for example organopolysiloxanes with the INCI name Phenyl Trimethicone, Trimethylsiloxyphenyl Dimethicone or Dimethylphenyl Dimethicone, or for example organopolysiloxanes with an organofunctional radical such as an aminopropyl, aminopropyl-aminoethyl, aminopropyl-aminoisobutyl radical, for example organopolysiloxanes with the INCI name Amodimethicone,
or for example organopolysiloxanes with a polyethylene glycol or polyalkylene glycol radical, for example organopolysiloxanes with the INCI name PEG-12 Dimethicone, PEG/PPG-25,25-Dimethicone or Cetyl PEG/PPG-15/15 Butyl Ether Dimethicone.

Further examples of organopolysiloxanes are silicone resins with the INCI names Trimethylsiloxysilicates or Polymethylsilsesquioxanes.

The cosmetic composition according to the invention comprises organopolysiloxanes and organopolysiloxane copolymers which are different from the precrosslinked organopolysiloxanes of the formula (I) present in the aqueous dispersions, preferably in amounts of from 0.1 to 40% by weight, preferably from 0.2 to 30% by weight, particularly preferably 0.3 to 20% by weight, in each case based on the total weight of the cosmetic composition.

Further preferred examples of conditioners are fatty acid esters and fatty acid alcohols.

Examples of fatty acid alcohols are alcohols with C8-C28 carbon chains such as the fatty alcohols 1-octadecanol with the INCI name Stearyl Alcohol, 1-hexadecanol with the INCI name Cetyl Alcohol, or fatty alcohols with the INCI names Cetearyl Alcohol, Myristyl Alcohol, Caprylic Alcohol, Lauryl Alcohol, Decyl Alcohol and Oleyl Alcohol. Besides conditioning properties, fatty acid alcohols also meet a structure-imparting, thickening effect in cosmetic compositions.

Further examples of fatty acid esters are esters of the fatty acids with the INCI name Palmitic Acid, Oleic Acid, Linolic Acid, Linoleic Acid, Caprylic Acid, Myristic Acid, Stearic Acid, for example fatty acid esters with the INCI name Isopropyl Palmitate, Ethylhexyl Palmitate, Isopropyl Myristate, Isopropyl Stearate.

The cosmetic composition according to the invention comprises fatty acid esters and fatty acid alcohols preferably in amounts of from 0.1 to 15% by weight, preferably from 0.3 to 12% by weight, especially preferably 0.5 to 10% by weight, in each case based on the total weight of the cosmetic composition.

Further preferred examples of conditioners are natural or synthetic oils and waxes.

Examples of preferred oils and waxes are hydrocarbons with linear or branched, saturated or unsaturated C4-C60 carbon chains, such as oils and waxes with the INCI names Isododecane, hydrated Polyisobutylene, hydrated Polydecene, Paraffin and Isoparaffin.

Further examples of preferred oils and waxes are carnauba wax, beeswax, wool wax, microcrystalline wax, jojoba oil, rice oil, calendula oil, sunflower oil, soybean oil, coconut oil, olive oil and almond oil.

The cosmetic composition according to the invention comprises oils and waxes preferably in amounts of from 0.1 to 10% by weight, preferably from 0.2 to 7% by weight, especially preferably 0.3 to 5% by weight, in each case based on the total weight of the cosmetic composition.

Further preferred examples of conditioners are panthenol, lipids, such as ceramides, proteins and hydrolyzed proteins, such as hydrolyzed collagen, hydrolyzed wheat proteins and hydrolyzed silk.

Optionally, the cosmetic composition comprises further cosmetically customary additives, such as e.g. surfactants, thickeners, gelling agents, film formers, moisturizing agents, UV filters, pearlescent pigments, vitamins, antioxidants, caffeine, antidandruff active ingredients or preservatives.

Examples of further additives customary in cosmetics and their INCI names are described in the "International Cosmetic Ingredient Dictionary & Handbook" of the Personal Care Product Council.

Optionally, the cosmetic composition comprises further cosmetically customary additives such as surfactants.

Examples of surfactants customary in cosmetics are also described in K. Schrader, A. Domsch, Cosmetology—Theory and Practice, Volume II, pages 11-8 to 11-22, Verlag für chemische Industrie, 2005, as well as in points 1 to 18 under examples of emulsifiers.

Examples of preferably used anionic surfactants correspond to the materials listed in points 1 to 3 under examples for anionic emulsifiers.

INCI names of preferably used anionic surfactants are, for example, Sodium Lauryl Sulfate, Ammonium Laureth Sulfate, Sodium Laureth Sulfate, Disodium 2-Sulfolaurate, Disodium Lauryl Sulfosuccinate or Disodium Laureth-Sulfosuccinate.

The cosmetic composition according to the invention comprises anionic surfactants preferably in amounts of from 1 to 30% by weight, preferably from 5 to 25% by weight, especially preferably 7 to 20% by weight, in each case based on the total weight of the cosmetic composition.

Examples of preferably used nonionic surfactants correspond to the materials listed in points 5 to 13 under examples of nonionic emulsifiers.

INCI names of preferably used nonionic surfactants are for example Coco Glucoside, Lauryl glucoside, Decyl Glucoside, PEG-40 Hydrogenated Castor Oil, Polysorbate 80 or PEG-7 Glyceryl Cocoate.

The cosmetic composition according to the invention comprises nonionic surfactants preferably in amounts of from 1 to 15% by weight, preferably from 2 to 12% by weight, especially preferably 3 to 10% by weight, in each case based on the total weight of the cosmetic composition.

Examples of preferably used amphoteric surfactants correspond to the materials listed in points 17 to 18 under examples of nonionic emulsifiers. Further preferred examples are compounds from the classes of alkylamidobetaines, alkylamphoacetates and alkylamphopropionates. INCI names of preferably used nonionic surfactants are, for example, Cocamidopropyl Betaine, Cetyl Betaine, Cocamide MEA, Cocamide DEA, Cocamide MIPA, Sodium Cocoamphoacetate and Sodium Cocoamphopropionate.

The cosmetic composition according to the invention comprises amphoteric surfactants preferably in amounts of from 1 to 15% by weight, preferably from 2 to 12% by weight, particularly preferably 3 to 10% by weight, in each case based on the total weight of the cosmetic composition.

Optionally, the cosmetic composition comprises further cosmetically customary additives such as thickeners.

Examples of preferably used thickeners are modified polysaccharides such as starch, cellulose, gum arabic and guar gums, e.g. polymers with the INCI names Cellulose Gum, Guar Gum, Xanthan Gum or *Cassia* Gum.

Further examples of thickeners are hydrophobically modified nonionic cellulose derivatives, e.g. the cellulose derivative with the INCI name Hydroxyethylcellulose.

Further examples of thickeners are crosslinked acrylic acid and methacrylic acid polymers and derivatives of crosslinked acrylic acid and methacrylic acid polymers, e.g. polymers with the INCI name Carbomer.

Further examples of thickeners are agents which, in combination with surfactants, achieve a thickening effect. Examples are monoglycerides of fatty acids, mono/diglycerides of ethoxylated fatty acids and ethoxylated fatty alcohols.

INCI names of preferably used thickeners which, in combination with surfactants, achieve a thickening effect are PEG-120 Methyl Glucose Dioleate, PEG-150 Distearate, Myristyl Glycol, PEG-200 Glyceryl Palmitate, Laureth-4 or PEG-200 Glyceryl Palmitate.

Further examples of thickeners are salts, e.g. salts with the INCI name Sodium Chloride.

The cosmetic composition according to the invention comprises thickeners preferably in amounts of from 0.1 to 10% by weight, in each case based on the total weight of the cosmetic composition.

Optionally, the cosmetic composition comprises further cosmetically customary additives such as film formers.

Preferred examples of film formers are polymers.

Examples of preferably used film-forming polymers are described in the "International Cosmetic Ingredient Dictionary & Handbook" of the Personal Care Product Council.

Examples of preferred film-forming polymers are acrylic acid polymer derivatives, acrylic acid copolymer derivatives, methacrylic acid derivatives and methacrylic acid copolymer derivatives.

Examples of preferred anionic polymers are copolymers of vinyl acetate and one or more acrylic acid, methacrylic acid monomers and esters thereof, e.g. polymers with the INCI name Acrylates/VA Copolymer.

Further examples of preferred film-forming polymers are copolymers of vinylpyrrolidones and one or more acrylic acid, methacrylic acid monomers and esters thereof, e.g. polymers with the INCI name Acrylates/VP Copolymer.

Further examples of preferred film-forming polymers are copolymers of tert-butyl acrylamide and one or more acrylic acid, methacrylic acid monomers and esters thereof, e.g. polymers with the INCI name Acrylates/t-Butylacrylamide Copolymer.

Further examples of preferred film-forming polymers are copolymers of vinyl acetate, crotonic acid and vinyl neodecanoate monomers, e.g. polymers with the INCI name VA/Crotonates/Vinyl Neodecanoate Copolymer.

Further examples of preferred film-forming polymers are copolymers of vinyl acetate, crotonic acid and vinyl neodecanoate monomers and vinylsilicones, e.g. polymers with the INCI name Crotonic Acid/Vinyl C8-C12 Isoalkyl Esters/VA/Bis-Vinyldimethicone Copolymer.

The cosmetic composition according to the invention comprises film-forming polymers preferably in amounts of from 0.1 to 15% by weight, preferably from 0.2 to 10% by weight, especially preferably 0.3 to 7% by weight, in each case based on the total weight of the cosmetic composition.

Optionally, the cosmetic composition comprises further cosmetically customary additives such as moisturizing agents.

Examples of preferably used moisturizing agents are glycerol, sorbitol, xylitol, polyethylene glycol, 1,2-propanediol, 1,3-propanediol or polypropylene glycol.

The cosmetic composition according to the invention comprises moisturizing agents preferably in amounts of from 0.1 to 10% by weight, preferably from 0.2 to 8% by weight, especially preferably 0.3 to 6% by weight, in each case based on the total weight of the cosmetic composition.

Optionally, the cosmetic composition comprises further cosmetically customary additives such as pearlizing agents.

Examples of preferably used pearlizing agents are pearlescent pigments or glycol distearate.

The cosmetic composition according to the invention comprises pearlizing agents preferably in amounts of amounts of from 0.1 to 7% by weight, preferably from 0.2 to 6% by weight, especially preferably 0.3 to 5% by weight, in each case based on the total weight of the cosmetic composition.

The invention further provides a process for the preparation of the cosmetic composition by mixing at least one aqueous dispersion according to the invention of precrosslinked organopolysiloxanes with at least one hair conditioning agent and optionally further cosmetically customary additives in a cosmetically acceptable medium.

The individual ingredients can be mixed together in a hot/hot, hot/cold or cold/cold process.

The addition of the dispersions according to the invention of precrosslinked organopolysiloxanes during the preparation of the cosmetic composition according to the invention takes place preferably at temperatures of at most 50° C., preferably at temperatures of at most 40° C., particularly preferably at temperatures of at most 35° C. It takes place preferably at temperatures of at least 5° C., preferably at temperatures of at least 10° C.

The cosmetic composition according to the invention can be present in the form of an emulsion, a suspension, a solution, a cream, a lotion, a foam, a stick, a paste, a gel.

The cosmetic composition according to the invention in the form of an emulsion can be present in the form of a W/O emulsion (water-in-oil emulsion), a O/W emulsion (oil-in-water emulsion) or as a multiple emulsion.

If the aim is to prepare a cosmetic composition comprising aqueous dispersion according to the invention of precrosslinked organopolysiloxanes in the form of an emulsion in translucent or transparent appearance, then preference is given to using aqueous dispersion according to the invention of precrosslinked organopolysiloxanes with particle sizes <60 nm, particularly preferably with particle sizes <50 nm, especially preferably with particle sizes <40 nm.

The invention further provides the use of the cosmetic composition according to the invention for treating keratin fibers, such as hair. Preferably, the cosmetic compositions are used for the cleaning and care of hair.

Examples of compositions for the cleaning and care of hair are hair shampoos, rinse-off conditioners, treatments, masks, sera, mousses, styling sprays, creams, gels, oils, end fluids and colorants.

EXAMPLES

Examples 1-6

Examples 1-6 below represent preparation processes for the synthesis of aqueous dispersions according to the invention of precrosslinked organopolysiloxanes for cosmetic compositions according to the invention.

The amine oils used in the examples are hydroxy-terminated or mixed hydroxy-methoxy-terminated.

Example 1

A dissolver model LDV 1 from PC Laborsystem is used to prepare a microemulsion with an average particle size of 20 to 50 nm from 6.5 g of isotridecyl pentaethoxylate, commercially available under the trade name Lutensol TO 5 (BASF), 20.0 g of a copolymer of 3-(2-aminoethylamino) propylmethylsiloxy and dimethylsiloxy units with an amine number of 0.13 and a viscosity of 3900 mm$^2$/s (at 25° C.), 2.9 g of glycerol, 0.12 g of 80% strength acetic acid, 0.19 g of N-morpholinomethyltriethoxysilane and 70 g of water. 0.13 g of phenoxyethanol, commercially available under the trade name S&M Phenoxyethanol (Schülke & Mayr GmbH & CO KG) is mixed into this emulsion.

Example 2

A dissolver model LDV 1 from PC Laborsystem is used to prepare a macroemulsion with an average particle size of 150 to 280 nm from 1.5 g of isotridecyl decaethoxylate, commercially available under the trade name Lutensol TO 109 (BASF), 35.0 g of a copolymer of 3-(2-aminoethylamino)propylmethylsiloxy and dimethylsiloxy units with an amine number of 0.16 and a viscosity of 4300 mm$^2$/s (at 25° C.), 0.16 g of 80% strength acetic acid, 0.37 g of N-morpholinomethyltriethoxysilane and 60 g of water. 0.13 g of phenoxyethanol, commercially available under the trade name S&M Phenoxyethanol (Schülke & Mayr GmbH & CO KG) is mixed into this emulsion.

Example 3

A dissolver model LDV 1 from PC Laborsystem is used to prepare a microemulsion with an average particle size of 20 to 60 nm from 6.0 g of isotridecyl pentaethoxylate, commercially available under the trade name Lutensol TO 5 (BASF), 1.5 g of isotridecyl decaethoxylate, commercially available under the trade name Lutensol TO 109 (BASF), 15.3 g of a copolymer of 3-(2-aminoethylamino)propyl-methylsiloxy and dimethylsiloxy units with an amine number of 0.26 and a viscosity of 1000 mm$^2$/s (at 25° C.), 3.6 g of glycerol, 0.25 g of 99% strength acetic acid, 0.30 g of N-morpholinomethyltriethoxysilane and 74.2 g of water. 0.9 g of phenoxyethanol, commercially available under the trade name S&M Phenoxyethanol (Schülke & Mayr GmbH & CO KG) is mixed into this emulsion.

After evaporating the emulsion over a period of 48 h/25° C., an elastic, gel-like material is left behind. 3 g of the elastic material produced in this way are not soluble in 7 g of toluene.

Example 4

A dissolver model LDV 1 from PC Laborsystem is used to prepare a macroemulsion from 6.1 g of isotridecyl decaethoxylate, commercially available under the trade name Lutensol TO 109 (BASF), 57.6 g of a polydimethylsiloxanediol with a content of terminal OH groups of 1100 ppm by weight, 18.4 g of PEG-400, commercially available under the trade name Polyglykol 400 (Clariant), 0.41 g of N-morpholinomethyltriethoxysilane and 17.3 g of water. 0.13 g of phenoxyethanol, commercially available under the trade name S&M Phenoxyethanol (Schülke & Mayr GmbH & CO KG) is mixed into this emulsion.

Example 5

A dissolver model LDV 1 from PC Laborsystem is used to prepare a macroemulsion from 6.1 g of isotridecyl decaethoxylate, commercially available under the trade name Lutensol TO 109 (BASF), 29.1 g of a polydimethylsiloxanediol with a content of terminal OH groups of 1100 ppm by weight, 28.9 g of a copolymer of 3-(2-aminoethylamino)propyl-methylsiloxy and dimethylsiloxy units with an amine number of 0.16 and a viscosity of 4300 mm$^2$/s (at 25° C.), 18.4 g of PEG-400, commercially available under the trade name Polyglykol 400 (Clariant), 0.43 g of N-morpholino-methyltriethoxysilane and 17.3 g of water. 0.13 g of phenoxyethanol, commercially available under the trade name S&M Phenoxyethanol (Schülke & Mayr GmbH & CO KG) is mixed into this emulsion.

Example 6

A dissolver model LDV 1 from PC Laborsystem is used to prepare a macroemulsion with an average particle size of 150 to 280 nm from 1.5 g of isotridecyl decaethoxylate, commercially available under the trade name Lutensol TO 109 (BASF), 35.1 g of a copolymer of 3-(2-aminoethylamino)propyl-methylsiloxy and dimethylsiloxy units with an amine number of 0.16 and a viscosity of 4300 mm$^2$/s (at 25° C.), 0.16 g of 80% strength acetic acid, 0.12 g of N-morpholinomethyltriethoxysilane, 0.22 g of N-morpholinomethyldiethoxysilane and 60 g of water. 0.13 g of phenoxyethanol, commercially available under the trade name S&M Phenoxyethanol (Schülke & Mayr GmbH & CO KG) is mixed into this emulsion.

Example 7

A dissolver model LDV 1 from PC Laborsystem is used to prepare a macroemulsion with an average particle size of 160 to 240 nm from 3.9 g of isotridecyl decaethoxylate, commercially available under the trade name Lutensol TO 109 (BASF), 35.1 g of a copolymer of 3-(2-aminoethylamino)propyl-methylsiloxy and dimethylsiloxy units with an amine number of 0.16 and a viscosity of 4300 mm$^2$/s (at 25° C.), 0.16 g of 80% strength acetic acid, 0.37 g of [(cyclohexylamino)methyl]triethoxysilane and 60 g of water. 0.13 g of phenoxyethanol, commercially available under the trade name S&M Phenoxyethanol (Schülke & Mayr GmbH & CO KG) is mixed into this emulsion.

Comparative Experiments V-1 to V-4

Comparative experiments V-1 to V-4 below represent preparation processes for the synthesis of aqueous dispersion of non-precrosslinked organopolysiloxanes for cosmetic compositions not according to the invention.

The amine oils used in the examples are hydroxy-terminated or mixed hydroxy-methoxy-terminated.

The procedure of examples 1-4 was repeated below, except that no N-morpholinomethyl-triethoxysilane is added, and therefore the organopolysiloxanes are not pre-crosslinked or uncrosslinked.

Comparative Experiment V-1

A dissolver model LDV 1 from PC Laborsystem is used to prepare a microemulsion with an average particle size of 20 to 50 nm from 6.5 g of isotridecyl pentaethoxylate, commercially available under the trade name Lutensol TO 5 (BASF), 20.5 g of a copolymer of 3-(2-aminoethylamino) propyl-methylsiloxy and dimethylsiloxy units with an amine number of 0.13 and a viscosity of 3900 mm$^2$/s (at 25° C.), 2.9 g of glycerol, 0.11 g of 80% strength acetic acid and 73.0 g of water. 0.13 g of phenoxyethanol, commercially available under the trade name S&M Phenoxyethanol (Schülke & Mayr GmbH & CO KG) is mixed into this emulsion.

Comparative Experiment V-2

A dissolver model LDV 1 from PC Laborsystem is used to prepare a macroemulsion with an average particle size of 150 to 280 nm from 1.5 g of isotridecyl decaethoxylate, commercially available under the trade name Lutensol TO 109(BASF), 35.0 g of a copolymer of 3-(2-aminoethyl-amino)propyl-methylsiloxy and dimethylsiloxy units with an amine number of 0.16 and a viscosity of 4300 mm$^2$/s (at 25° C.), 0.16 g of 80% strength acetic acid and 62.0 g of water. 0.13 g of phenoxyethanol, commercially available under the trade name S&M Phenoxyethanol (Schülke & Mayr GmbH & CO KG) is mixed into this emulsion.

Comparative Experiment V-3

A dissolver model LDV 1 from PC Laborsystem is used to prepare a microemulsion with an average particle size of 20 to 60 nm from 6.0 g of isotridecyl pentaethoxylate, commercially available under the trade name Lutensol TO 5 (BASF), 1.2 g of isotridecyl decaethoxylate, commercially available under the trade name Lutensol TO 109 (BASF), 15.3 g of a copolymer of 3-(2-aminoethylamino)propyl-methylsiloxy and dimethylsiloxy units with an amine number of 0.26 and a viscosity of 1000 mm$^2$/s (at 25° C.), 3.6 g of glycerol, 0.25 g of 99% strength acetic acid and 76.5 g of water. 0.9 g of phenoxyethanol, commercially available under the trade name S&M Phenoxyethanol (Schülke & Mayr GmbH & CO KG) is mixed into this emulsion.

After evaporating the emulsion over a period of 48 h/25° C., a cloudy, high-viscosity oil is left behind. 3 g of the oil produced in this way are soluble in 7 g of toluene.

Comparative Experiment V-4

A dissolver model LDV 1 from PC Laborsystem is used to prepare a macroemulsion from 6.1 g of isotridecyl decaethoxylate, commercially available under the trade name Lutensol TO 109 (BASF), 57.6 g of a polydimethyl-siloxanediol with a content of terminal OH groups of 1100 ppm by weight, 18.4 g of PEG-400, commercially available under the trade name Polyglykol 400 (Clariant) and 18.0 g of water. 0.13 g of phenoxyethanol, commercially available under the trade name S&M Phenoxyethanol (Schülke & Mayr GmbH & CO KG) is mixed into this emulsion.

Test Methods:

Test methods for assessing the effect of cosmetic compositions: the assessment of the application behavior of the cosmetic composition and its effect with regard to wetting with water/hydrophobicization, combing force, softness and color protection on keratin fibers was performed on Caucasian hair.

All hair tresses were cleaned prior to use. For this, the hair tresses are placed for 24 hours into a solvent mixture of equal parts of acetone, ethanol, isopropanol and completely demineralized water. After removing the solvent mixture, the hair tresses are thoroughly washed with completely demineralized water. Then, each hair tress is washed with 3 ml of an ammonium lauryl sulfate solution (25%), STEPANOL® ALS 25, STEPAN Company, and rinsed with completely demineralized water until lather was no longer visible (at least 2 minutes). After the basic cleaning, the tresses are conditioned prior to being used further for at least 12 hours at 23° C. and 60% humidity.

Wetting with Water—Hydrophobicity of Hair:

The measurement principle for determining the hydrophobicity of hair follows the procedures in DE 198 26 081 A1 and DE 10 2010 035 844. The wetting behavior of keratin fibers with water was determined on hair tresses. For this purpose, hair tresses from a supply of damaged, Caucasian hair from Kerling International Haarfabrik GmbH (hair tress degree of damage B, double-drawn) with a weight of 2 g and a length of 20 cm were used—optionally untreated or treated with a cosmetic composition. The hair tress to be analyzed was divided, from the direction of hair root to hair tip, into part sections each 2 cm in length, and prepared by surrounding the part sections of the hair tress with a plastic tube with a diameter of about 0.5 cm. The part sections comprising the hair root and hair tip are discarded. The other prepared sample bodies were transferred at the same time to a sample holder in a basin filled with deionized water heated to 25° C. The sample holder is constructed in a way to position the samples at the same level and perpendicular to the bottom of the basin. The sample bodies are prevented from rising as a result of inflation forces by virtue of the sample holder. A resistant-free sinking of the sample bodies onto the bottom of the basin is ensured by virtue of the sample holder. After introducing the sample bodies into the water basin, the hair surrounded by the plastic tube was wetted with water. When the hair surface was adequately wetted with water, the respective sample body sank from the sample holder to the bottom of the basin. The time until the sample body sinks correlates with the hydrophobicity of the hair surface and, the more hydrophobic the hair surface, the longer it is. The time until the sample bodies sink in seconds was ascertained and correlated as a measure of the hydrophobicity of the hair surface. At least three hair tresses were assessed per measurement. The measurement result used was the average value of the sample bodies over all of the measured hair tresses.

Combing Force Measurement:

To determine the combing force of wet and dry hair, hair tresses from damaged, Caucasian hair from Kerling International Haarfabrik GmbH (hair tresses degree of damage B, double-drawn) with a weight of 2 g and a length of 20 cm were used.

Combing force was measured with the double combing method in accordance with Y. K. Kamath and Hans-Dietrich Weigmann, J. Soc. Cosmet. Chem., 37, 111-124, 1986 using an Instron 3343 load-elongation machine.

Firstly, the wet and dry combing force along the measurement stretch of untreated hair tresses is determined. The hair tresses are then treated with a cosmetic composition according to the invention and the force uptake during the combing operation is determined.

The measurement value given is the reduction in the combing force along the measurement stretch (work) which arises between the treated and untreated hair tress. The average from three hair tresses is calculated. The combing force reduction is given as a percentage.

Softness:

The measurement principle for determining the hydrophobicity of hair follows the procedures in DE 10 2010 020 192. To determine the softness of the hair, hair tresses of damaged, Caucasian hair from Kerling International Haarfabrik GmbH (hair tresses degree of damage B, double-drawn) with a weight of 2 g and a length of 20 cm were used. The hair softness in the dry state was determined using an Instron 3343 load-testing machine by correlating the required tensile force with the parameters flexural rigidity and surface roughness of the hair bundle. These two parameters in turn correlate with the hair softness. For this purpose, an untreated hair tress was clamped in a measurement arrangement consisting of five oppositely displaced rods. The shape of the hair tress in this starting position is a type of double S. Following this preparation, the hair tress is pulled in one direction from the measurement arrangement and the required force along the measurement stretch is evaluated as work. The hair tresses are then treated with a cosmetic composition according to the invention and the force uptake upon drawing the hair tress through the measurement arrangement along the measurement stretch is determined. The measurement value given is the reduction in tensile force along the measurement stretch (work) which arises between the treated and untreated hair tress. A high reduction in tensile force (work) corresponds to a good soft feel. The average value from three hair tresses is calculated.

Washing Procedure Shampoo:

0.1 g of shampoo per g of hair is applied to a cleaned, wetted hair tress. The shampoo is massaged in for 30 seconds in the direction of the hair tips. The hair tress is then rinsed for 30 s under running, completely demineralized water and detangled using a large-toothed comb. The procedure is repeated twice. On the last occasion, the rinsing process is extended to 60 s. The hair tress is then dried for at least 12 h at a humidity of 60% and a temperature of 23° C.

Washing Procedure Conditioner:

0.5 g of rinse-off conditioner/g of hair is applied to a cleaned, wetted hair tress. The rinse-off conditioner is massaged in for 120 seconds in the direction of the hair tips. The hair tress is then rinsed for 60 s under running, completely demineralized water and detangled using a large-toothed comb. The procedure is repeated. The hair tress is then dried for at least 12 h at a humidity of 60% and a temperature of 23° C.

Color Protection/Color Measurement:

An assessment of the cosmetic composition according to the invention as regards the color protection effect on keratin fibers was carried out on colored real hair. For this purpose, hair tresses with a weight of 4 g and a length of 20 cm of damaged, Caucasian hair from Kerling International Haarfabrik GmbH were used (adhesive tress tight made of European hair, bleaching stage A, mixture 79). The hair tresses were colored red. The color shade used was Majirouge 6.66 from L'Oreal. 50 ml of the hair coloring paste were mixed with 80 ml of a six percent hydrogen peroxide solution. The paste was applied evenly to the hair tresses. After a contact time of 40 minutes at room temperature, the coloring paste was washed out of the hair tresses. After treating the hair tress with a surfactant solution (STEPANOL® ALS 25 diluted to 5% active content, STEPAN Company) and drying the tresses, the dyeing operation was repeated.

The color measurement is performed on the smooth surface of the hair bundle using the color measuring instrument Spectro Guide from Byk-Gardner. The color parameters L, a, b (Lab color space) are recorded.

Assessment of the color protection as a result of a hair treatment with cosmetic compositions according to the invention:

Colored hair changes the color impression by washing with shampoo. The change in color impression after a wash cycle can be described by the ΔE value, which is defined as:

$$\Delta E = ((L1-Lo)^2 + (a1-a0)^2 + (b1-b0)^2)^{1/2}$$

L0, a0, b0 are the color values of a colored, untreated hair bundle.

L1, a1 and b1 are the color values of the hair bundle after the wash cycle.

A wash cycle is defined as follows:

A hair bundle is treated with a cosmetic composition according to the invention, followed by two shampoo washes using a commercial, silicone-free shampoo.

The treatment with a cosmetic composition according to the invention can take place in the form of a leave-in product or a rinse-off product.

Measurement of the Color Protection Effect:

After 1, 2, 3 and 4 wash cycles, the ΔE value is ascertained in each case compared to the reference value. The control used is a hair bundle which is treated with a cosmetic composition between the shampoo washes, said composition differing from the composition according to the invention only by virtue of the fact that it comprises no dispersion of precrosslinked organopolysiloxanes.

A larger ΔE value is an indication of a greater color change.

The color protection effect can be expressed using the following formula as an improvement of the ΔE value:

$$\% \text{ color protection corresponds to } \% \Delta E \text{ improvement} = ((\Delta E(\text{treated}) - \Delta E(\text{control}))/\Delta E(\text{control})) \times 100$$

Curl Retention:

In this method for determining the hair setting, the percentage changes from starting length to end length of curls prepared in a defined manner are recorded compared to the hair tress length.

Hair bundles are prepared from undamaged, Caucasian hair from Kerling International Haarfabrik GmbH. Hair tresses with a length of 15 cm and a weight of 3.5 g are bound in each case with a binding thread and fixed permanently using a suitable adhesive. The hair tresses are cleaned using shampoo and rinsed with completely demineralized water. The hair tresses are combed, wound onto a plastic rod with a diameter of 1.1 cm, temporarily set with a covering and dried overnight at 50° C. The curls are stripped off from the plastic rods and then treated with the cosmetic composition according to the invention. After a drying phase of one hour at room temperature, the curls are attached to a graduated hanging device in a climatically controlled cabinet at 23° C. and 90% relative humidity. The starting length of the curl was determined and noted beforehand. At certain time intervals, the curl length is read off as a change relative to the starting length over a period of 24 h. The curl retention is given as a percentage change compared with the starting position. A high value for the curl retention means good hold or good setting.

Hereinbelow, all data in parts refer to parts by weight.

Examples 8A to 8E

Cosmetic Composition

Rinse-Off Conditioner (Rinse)

The examples below represent cosmetic compositions comprising—in a cosmetically acceptable medium—at least one hair conditioning agent and at least one aqueous dispersion of precrosslinked organopolysiloxanes from examples 1 to 7. The active content of organopolysiloxane in the cosmetic composition is 2% by weight.

TABLE 1a

Rinse-off conditioner formulation 8A to 8E.
Data in parts by weight.

| Constituents (INCI name) | Ex. 8A | Ex. 8B | Ex. 8C | Ex. 8D | Ex. 8E |
|---|---|---|---|---|---|
| Water | ad 100 | ad 100 | ad 100 | ad 100 | ad 100 |
| Hydroxyethyl-cellulose [1] | 1.2 | 1.2 | 1.2 | 1.2 | 1.2 |
| Cetyl Alcohol [2] | 1.0 | 1.0 | 1.0 | 1.0 | 1.0 |
| Polysorbate 80 [3] | 1.0 | 1.0 | 1.0 | 1.0 | 1.0 |
| Behentrimonium Chloride [4] | 1.8 | 1.8 | 1.8 | 1.8 | 1.8 |
| Stearamidopropyl Dimethylamine [5] | 0.5 | 0.5 | 0.5 | 0.5 | 0.5 |
| Stearyl Alcohol [6] | 3.0 | 3.0 | 3.0 | 3.0 | 3.0 |
| Citric Acid [7] | 0.2 | 0.2 | 0.2 | 0.2 | 0.2 |
| Tetrasodium EDTA [8] | 0.2 | 0.2 | 0.2 | 0.2 | 0.2 |
| Emulsion from Example 1 | 10.0 | | | | |
| Emulsion from Example 2 | | 5.7 | | | |
| Emulsion from Example 3 | | | 13.3 | | |
| Emulsion from Example 4 | | | | 3.3 | |
| Emulsion from Example 5 | | | | | 3.0 |
| Methylchloroisothiazolinone and Methylisothiazolinone [9] | 0.1 | 0.1 | 0.1 | 0.1 | 0.1 |

The raw materials are available under the following trade names:
[1] Hydroxyethylcellulose: Tylose ® H 4000 P2, Shin-Etsu Chem. Co.
[2] Cetyl alcohol: Cetyl alcohol, Merck KGaA
[3] Polysorbate 80: Tween ™ 80, Croda GmbH
[4] Behentrimonium chloride: Genamin ® KDMP, Clariant GmbH
[5] Stearamidopropyl Dimethylamine, Incromine ™ SB, Croda GmbH
[6] Stearyl alcohol: Stearyl alcohol Merck KGaA
[7] Citric Acid: Citric Acid, Sigma
[8] Tetrasodium EDTA: EDETA ® B Powder, BASF Corporation
[9] Methylchloroisothiazolinone and methylisothiazolinone: Kathon ™ CG, Rohm and Haas Company, Inc.

Preparation Instructions:

Water is introduced and heated to 75° C. with stirring. During this, 1.2 parts of hydroxyethylcellulose are added. When 65° C. is reached, 0.5 parts of stearamidopropyl dimethylamine, 1 part of polysorbate 80, 3 parts of stearyl alcohol, 1 part of cetyl alcohol and 1.8 parts of behentrimonium chloride are added. The mixture is stirred until 75° C. is reached and the ingredients are in dissolved form. The mixture is then cooled. During cooling, 0.2 parts of citric acid and 0.2 parts of tetrasodium EDTA are added. At 35° C., 0.1 parts of methylchloroisothiazolinone/methylisothiazolinone are added. The emulsion from the examples is added with further stirring. The formulation is homogenized for 15 minutes with stirring.

Comparative Experiments V-5A to V-5D

Cosmetic Composition: Rinse-Off Conditioner (Rinse)

The comparative experiments 5A-5D below represent non-inventive cosmetic compositions comprising—in a cosmetically acceptable medium—at least one conditioning agent and an aqueous dispersion of a non-precrosslinked organopolysiloxane. The active content of organopolysiloxane is 2% by weight.

In the preparation of the cosmetic compositions corresponding to the comparative experiments V5A-V5D, the procedure of examples 8A-8D was subsequently repeated except that instead of the emulsions from example 1-4 (emulsions of precrosslinked organopolysiloxanes according to the invention), the emulsions of comparative experiments V1-V4 are used. Emulsions of comparative experiments V1-V4 contain organopolysiloxanes that are analogous to examples 1-4 as regards starting viscosity and amine number, but they are uncrosslinked.

TABLE 1b

Rinse-off conditioner formulation V5A to V5D.
Data in parts by weight.

| Constituents (INCI name) | Comp. Experiment V-5A | Comp. Experiment V-5B | Comp. Experiment V-5C | Comp. Experiment V-5D |
|---|---|---|---|---|
| Water | ad 100 | ad 100 | ad 100 | ad 100 |
| Hydroxyethyl-cellulose [1] | 1.2 | 1.2 | 1.2 | 1.2 |
| Cetyl Alcohol [2] | 1.0 | 1.0 | 1.0 | 1.0 |
| Polysorbate 80 [3] | 1.0 | 1.0 | 1.0 | 1.0 |
| Behentrimonium Chloride [4] | 1.8 | 1.8 | 1.8 | 1.8 |
| Stearamidopropyl Dimethylamine [5] | 0.5 | 0.5 | 0.5 | 0.5 |
| Stearyl Alcohol [6] | 3.0 | 3.0 | 3.0 | 3.0 |
| Citric Acid [7] | 0.2 | 0.2 | 0.2 | 0.2 |
| Tetrasodium EDTA [8] | 0.2 | 0.2 | 0.2 | 0.2 |
| Emulsion from comparative experiment V-1 | 10.0 | | | |
| Emulsion from comparative experiment V-2 | | 5.7 | | |
| Emulsion from comparative experiment V-3 | | | 13.3 | |
| Emulsion from comparative experiment V-4 | | | | 3.0 |
| Methylchloroisothiazolinone and Methylisothiazolinone [9] | | 0.1 | 0.1 | 0.1 |

The raw materials are available under the following trade names:
[1] Hydroxyethylcellulose: Tylose ® H 4000 P2, Shin-Etsu Chemical Co.
[2] Cetyl alcohol: Cetyl alcohol, Merck KGaA
[3] Polysorbate 80: Tween ™ 80, Croda GmbH
[4] Behentrimonium chloride: Genamin ® KDMP, Clariant GmbH
[5] Stearamidopropyl Dimethylamine, Incromine ™ SB, Croda GmbH
[6] Stearyl alcohol: Stearyl alcohol Merck KGaA
[7] Citric Acid: Citric Acid, Sigma
[8] Tetrasodium EDTA: EDETA ® B Powder, BASF Corporation
[9] Methylchloroisothiazolinone and methylisothiazolinone: Kathon ™ CG, Rohm and Haas Company, Inc.

Preparation Instructions:

Water is introduced and heated to 75° C. with stirring. During this, 1.2 parts of hydroxyethylcellulose are added. When 65° C. is reached, 0.5 parts of stearamidopropyl dimethylamine, 1 part of polysorbate 80, 3 parts of stearyl alcohol, 1 part of cetyl alcohol and 1.8 parts of behentrimonium chloride are added. The mixture is stirred until 75° C. is reached and the ingredients are in dissolved form. The mixture is then cooled. During cooling, 0.2 parts of citric acid and 0.2 parts of tetrasodium EDTA are added. At 35° C., 0.1 parts of methylchloroisothiazolinone/methylisothiazolinone are added. The emulsion from the comparative experiments V-5A to V-5D is added with further stirring. The formulation is homogenized for 15 minutes with stirring.

Comparison of the Rinse-Off Conditioners of Examples 8A-8D According to the Invention with the Comparative Experiments V-5A to V-5D.

The examples and comparative experiments listed differ in that in the case of examples 8A-8D aqueous dispersions of precrosslinked organopolysiloxanes were used, in comparative experiment V-5A to V-5D in each case analogous aqueous dispersions of the corresponding non-precrosslinked organopolysiloxanes. In the direct comparison, the following examples/comparative experiments correlate:

Example 8A—Comparative experiment V-5A

Example 8B—Comparative experiment V-5B

Example 8C—Comparative experiment V-5C

Example 8D—Comparative experiment V-5D

Hydrophobicity, Wettability of Hair

Undamaged, natural hair has an intact protective lipid layer on the hair surface and therefore has high hydrophobicity. The hydrophobicity of the hair surface decreases with increasing degree of damage to the hair since, as a result of the hair surface being destroyed, the water-repelling protective lipid layer along the hair fiber becomes damaged and hydrophilic, amino-acid-based structures increasingly act as the hair surface. The hair hydrophobicity can be quantified by measuring the time until the sample bodies sink in accordance with the method description "Wetting with water—hydrophobicity of hair". Table 2 shows the measurement values for undamaged and damaged Caucasian hair. Increasing hair damage is typically accompanied by loss of cosmetic properties such as e.g. smoothness, softness, shine or color impression.

TABLE 2

Results of the wettability of undamaged (natural) and damaged hair tresses/hydrophobicization by correlation of the hair hydrophobicity with the time until the sample bodies sink in accordance with the description "Wetting with water - hydrophobicity of hair".

|  | Untreated, undamaged Caucasian hair[1] | Untreated, damaged Caucasian hair[2] |
|---|---|---|
| Time until the sample bodies sink [s] | 700 | 1 |

[1]Kerling International Haarfabrik GmbH (undamaged hair)
[2]Kerling International Haarfabrik GmbH (hair tresses degree of damage B)

The treatment of damaged hair with rinse-off conditioners leads to the formation of a protective film on the hair surface which increases the hydrophobicity compared to untreated, damaged hair. As hydrophobicity increases, cosmetic parameters such as e.g. smoothness, softness, shine or color impression also improve. The increase in hydrophobicity is dependent on the type of organopolysiloxane used in the rinse-off conditioner for the examples and comparative experiments discussed below. For example, the hydrophobicizing effect of rinse-off conditioners comprising aqueous dispersions of amino-functionalized polydimethylsiloxanes is greater than for rinse-off conditioners comprising aqueous dispersions of polydimethylsiloxanes.

In all cases, the use of aqueous dispersions of precrosslinked organopolysiloxanes (synthesis description in Example 1-4) leads to a higher hydrophobicization than when using aqueous dispersions of the corresponding uncrosslinked organopolysiloxanes (synthesis description in comparative experiments 1-4) as a constituent of the rinse-off conditioners. An overview of the individual experimental results for quantifying the hydrophobicity can be found in tables 3-6.

TABLE 3

Rinse-off conditioner/results of the wettability of the hair tresses/hydrophobicization following treatment with rinse-off conditioners by correlation of the hair hydrophobicity with the time until the sample bodies sink in accordance with the description "Wetting with water - hydrophobicity of hair".

|  | Example 8A | Comparative experiment V-5A |
|---|---|---|
| Time until the sample bodies sink [s] | 276 | 227 |

The treatment of hair tresses with a rinse-off conditioner comprising a microemulsion of a precrosslinked amino-functional silicone oil with the amine number 0.13 (example 8A) leads to a higher hydrophobicity of the hair compared to the treatment with a rinse-off conditioner which has a microemulsion of an analogous, non-precrosslinked amino-functional silicone oil as constituent (comparative experiment V-5A).

TABLE 4

Rinse-off conditioner/results of the wettability of the hair tresses/hydrophobicization following treatment with rinse-off conditioner by correlation of the hair hydrophobicity with the time until the sample bodies sink in accordance with the description "Wetting with water - hydrophobicity of hair".

|  | Example 8B | Comparative experiment V-5B |
|---|---|---|
| Time until the sample bodies sink [s] | 235 | 164 |

The treatment of hair tresses with a rinse-off conditioner comprising a macroemulsion of a precrosslinked amino-functional silicone oil with the amine number 0.16 (example 8B) leads to a higher hydrophobicity of the hair compared to the treatment with a rinse-off conditioner which has a macroemulsion of an analogous, non-precrosslinked amino-functional silicone oil as constituent (comparative experiment V-5B).

TABLE 5

Rinse-off conditioner/results of the wettability of the hair tresses/hydrophobicization following treatment with rinse-off conditioner by correlation of the hair hydrophobicity with the time until the sample bodies sink in accordance with the description "Wetting with water - hydrophobicity of hair".

|  | Example 8C | Comparative experiment V-5C |
|---|---|---|
| Time until the sample bodies sink [s] | 1311 | 783 |

The treatment of hair tresses with a rinse-off conditioner comprising a microemulsion of a precrosslinked amino-functional silicone oil with the amine number 0.26 (example 8C) leads to a higher hydrophobicity of the hair compared to the treatment with a rinse-off conditioner which has a microemulsion of an analogous, non-precrosslinked amino-functional silicone oil as constituent (comparative experiment V-5C).

TABLE 6

Rinse-off conditioner/results of the wettability of the hair tresses/hydrophobicization following treatment with rinse-off conditioner by correlation of the hair hydrophobicity with the time until the sample bodies sink in accordance with the description "Wetting with water - hydrophobicity of hair".

|  | Example 8D | Comparative experiment V-5D |
|---|---|---|
| Time until the sample bodies sink [s] | 31 | 19 |

The treatment of hair tresses with a rinse-off conditioner comprising a microemulsion of a precrosslinked silicone oil (example 8D) leads to a higher hydrophobicity of the hair compared to the treatment with a rinse-off conditioner which has a microemulsion of an analogous, non-precrosslinked silicone oil as constituent (comparative experiment V-5D). Example 8D and comparative experiment 5D clearly show that the hydrophobicity of the treated hair is considerably lower when using silicone oils in the rinse-off conditioner as active component than when using amino-functionalized silicone oils (example 8A-8C).

In all cases, a higher hydrophobicity can be attained by using rinse-off conditioners comprising aqueous dispersions of precrosslinked organopolysiloxanes than when using the aqueous dispersions of the analogous, non-precrosslinked organopolysiloxanes.

The use of the aqueous dispersions of precrosslinked organopolysiloxanes in the rinse-off conditioner, moreover, leads to a significant improvement in conditioning properties, such as e.g. the reduction in combing forces in the wet and dry state, or an increase in the softness of the hair. Furthermore, a positive effect arises as regards the color resistance of colored hair to shampoo washes. The results are listed below for the rinse-off conditioners of examples 8A-8E.

TABLE 7

Rinse-off conditioner/results of the dry combing force reduction and wet combing force reduction and improvement in the softness following treatment with a rinse-off conditioner according to the invention. All results relate to the comparison to untreated hair tresses.

| Ex. | Reduction in dry combing force [%] | Reduction in wet combing force [%] | Improvement in softness [%] |
|---|---|---|---|
| 8A | 76 | 92 | 54 |
| 8B | 55 | 91 | 40 |
| 8C | 46 | 85 | 46 |
| 8D | 61 | 91 | 33 |
| 8E | 17 | 77 | 22 |

In all cases, a significant reduction in the wet combing force and dry combing force of the hair tresses can be measured as a result of treatment with a rinse-off conditioner comprising an aqueous emulsion of a precrosslinked organopolysiloxane, said reduction being linked to a significant improvement in hair softness.

TABLE 8

Rinse-off conditioner/results of the color protection measurements following use of a rinse-off conditioner according to the invention. All results compare to the blank value after four washing cycles.

| Ex. | Improvement in comparison to the blank value [%] |
|---|---|
| 8A | 9 |
| 8B | 10 |
| 8C | 10 |
| 8D | 8 |

In all cases, the rate at which the red hair color is washed out can be slowed as a result of treatment with a rinse-off conditioner comprising an aqueous emulsion of a precrosslinked organopolysiloxane. Compared to treating the hair tresses with a conditioner comprising no aqueous emulsion of a precrosslinked organopolysiloxane, there is an improvement between 8 and 10 percent after four wash cycles. For details on assessing the parameters and the experiment procedure, see the method description "color protection/color measurement".

For comparison, table 9 shows the results for the dry combing force reduction and wet combing force reduction after using rinse-off conditioners not in accordance with the invention comprising aqueous emulsions of non-precrosslinked organopolysiloxanes.

TABLE 9

Results of the dry combing force reduction and wet combing force reduction of non-inventive rinse-off conditioners. All results compared to untreated hair tresses.

| Comparative experiment | Reduction in dry combing force [%] | Reduction in wet combing force [%] |
|---|---|---|
| V-5A | 75 | 87 |
| V-5B | 51 | 85 |
| V-5C | 42 | 81 |
| V-5D | 5 | 83 |

The improvements for dry and wet combing force tend to be greater (table 7) when using dispersions of precrosslinked organopolysiloxanes in rinse-off conditioners than when using the corresponding dispersions of non-precrosslinked organopolysiloxanes (table 9).

Examples 9A/9B to Example 13

The examples below represent cosmetic compositions comprising—in a cosmetically acceptable medium—at least one conditioning agent and at least one aqueous dispersion of precrosslinked organopolysiloxanes from examples 1 to 7. The active content of organopolysiloxane in the cosmetic composition is 2% by weight.

Example 9A and 9B

Cosmetic Composition

2-Phase Conditioner

TABLE 10

2-Phase leave-in conditioner formulations 9A and 9B. Data in parts by weight.

| Constituents (INCI name) | Ex. 9A | Ex. 9B |
|---|---|---|
| Aqua (water, DEM.) | ad 100 | ad 100 |
| Dimethicone.[1] | 15.0 | 15.0 |
| Propylene glycol, Diazolidinyl urea, Methylparaben, Propylparaben[2] | 1.0 | 1.0 |
| Sodium chloride[3] | 4.0 | 4.0 |
| Emulsion from Example 1 | 3.0 | |
| Emulsion from Example 6 | | 1.7 |

[1] Dimethicone: Wacker-Belsil ® DM 1 plus, Wacker-Chemie AG
[2] Propylene Glycol, Diazolidinyl Urea, Methylparaben, Propylparaben: Germaben ® II, International Specialty Products
[3] 25 percent strength solution Preparation Instructions:

Water is introduced. It is heated to 35° C., then sodium chloride is added with stirring. Following complete dissolution of sodium chloride, propylene glycol, diazolidinyl urea, methylparaben, propylparaben are added, the mixture is cooled to room temperature, and, with stirring, the emulsion from the examples is added. Finally, the mixture is combined with dimethicone. This gives a two-phase system which can be mixed with vigorous shaking and separates into two phases again after a certain amount of time.

The 2-phase conditioner-treated hair was assessed in a panel test as being very soft, silky and easy to comb.

Example 10

Cosmetic Composition

Shampoo

TABLE 11

Shampoo formulations 10A-10D. Data in parts by weight.

| Constituents (INCI name) | Ex. 10A | Ex. 10B | Ex. 10C | Ex. 10D |
|---|---|---|---|---|
| Aqua (water, DEM.) | ad 100 | ad 100 | ad 100 | ad 100 |
| Guar hydroxypropyltrimonium chloride[1] | 0.20 | 0.20 | 0.20 | 0.20 |
| Sodium laureth sulfate[2] | 41.50 | 41.50 | 41.50 | 41.50 |
| Glycol distearate[3] | 1.20 | 1.20 | 1.20 | 1.20 |
| PEG-150 distearate[4] | 0.20 | 0.20 | 0.20 | 0.20 |
| Emulsion from Example 1 | 10.0 | | | |
| Emulsion from Example 2 | | 5.7 | | |
| Emulsion from Example 3 | | | 13.3 | |
| Emulsion from Example 4 | | | | 3.3 |
| Cocamidopropyl betaine[5] | 13.42 | 13.42 | 13.42 | 13.42 |
| Methylchloroisothiazolinone and Methylisothiazolinone[6] | 0.06 | 0.06 | 0.06 | 0.06 |
| Sodium chloride[7] | 0.45 | 0.45 | 0.45 | 0.45 |

[1] Guar Hydroxypropyltrimonium Chloride: N-Hance ® 3000, Hercules Inc.
[2] Sodium Laureth Sulfate: Genapol ® LRO 26.5%, Clariant GmbH
[3] Glycol Distearate: Genapol ® PMS, Clariant GmbH
[4] PEG-150 Distearate: Emulgin ® EO 33, Cognis Deutschland GmbH
[5] Cocamidopropyl Betaine: Genagen ® CAB 30%, Clariant GmbH
[6] Methylchloroisothiazolinone and Methylisothiazolinone: Kathon ™ CG, Rohm and Haas Company, Inc
[7] 25 percent strength solution Preparation Instructions:

0.2 parts of guar hydroxypropyltrimonium chloride are dispersed in water. 41.5 parts of sodium laureth sulfate are slowly stirred in and the mixture is heated to 75° C. in stages. During the heating, 0.2 parts of PEG-150 distearate are added at 50° C., and at 65° C. 1.2 parts of glycol distearate are added.

The mixture is then cooled. Upon reaching 35° C., 0.06 parts of methylchloroisothiazolinone/methylisothiazolinone and the emulsion corresponding to the examples are added and the mixture is stirred for 5 minutes. Finally, 13.4 parts of cocamidopropyl betaine and 0.5 parts of sodium chloride are added and stirring is carried out in each case for 10 minutes.

TABLE 12

Shampoo/results of the dry combing force reduction and wet combing force reduction. Improvement in softness. All results compared to untreated hair tresses.

| Ex. | Reduction in dry combing force [%] | Reduction in wet combing force [%] | Improvement in softness [%] |
|---|---|---|---|
| 10A | 51 | 83 | 50 |
| 10B | 64 | 57 | 36 |
| 10C | 60 | 31 | 23 |
| 10D | 27 | 51 | 20 |

Example 11

Cosmetic Composition

Shampoo

TABLE 13

Shampoo formulations 11A and 11B. Data in parts by weight.

| Constituents (INCI name) | Ex. 11A | Ex. 11B |
|---|---|---|
| Aqua (water, DEM.) | ad 100 | ad 100 |
| Polyquaternium-10[1] | 0.10 | 0.10 |
| Sodium Laureth Sulfate[2] | 71.60 | 67.9 |
| Glycol Distearate[3] | 1.20 | 1.20 |
| Hydroxyethylcellulose[4] | 0.20 | 0.20 |
| Emulsion from Example 1 | 10.0 | |
| Emulsion from Example 7 | | 13.3 |
| Cocamidopropyl Betaine[5] | 10.0 | 8.3 |
| Methylchloroisothiazolinone | 0.06 | 0.06 |

TABLE 13-continued

Shampoo formulations 11A and 11B.
Data in parts by weight.

| Constituents (INCI name) | Ex. 11A | Ex. 11B |
|---|---|---|
| and Methylisothiazolinone[6] | | |
| Sodium Chloride[7] | 0.5 | 1.0 |

[1] Polyquaternium-10: Ucare ™ Polymer JR-400, Amerchol Corporation
[2] Sodium Laureth Sulfate: Genapol ® LRO 26.5%, Clariant GmbH
[3] Glycol Distearate: Genapol ® PMS, Clariant GmbH
[4] Hydroxyethylcellulose: Tylose ® H 4000 P2, Shin-Etsu Chemical Co
[5] Cocamidopropyl Betaine: Genagen ® CAB 30%, Clariant GmbH
[6] Methylchloroisothiazolinone and Methylisothiazolinone: Kathon ™ CG, Rohm and Haas Company, Inc
[7] 25 percent strength solution Preparation Instructions:

0.1 parts of polyquaternium-10 are dispersed in water. Sodium laureth sulfate is stirred in slowly and the mixture is heated to 75° C. Upon reaching 50° C., 0.2 parts of hydroxyethylcellulose are added, and at 65° C. 1.2 parts of glycol distearate are added. The mixture is stirred until 75° C. is reached. The mixture is then cooled. Upon reaching 35° C., 0.06 parts of methylchloroisothiazolinone/methylisothiazolinone and the emulsion corresponding to the examples are added and the mixture is stirred for 5 minutes. Finally, cocamidopropyl betaine and sodium chloride solution is added and stirring is carried out in each case for 10 minutes.

TABLE 14

Shampoo/result of the dry combing force reduction and wet combing force reduction. Improvement in softness. All results compared to untreated hair tresses.

| Ex. | Reduction in dry combing force [%] | Reduction in wet combing force [%] | Improvement in softness [%] |
|---|---|---|---|
| 11A | 55 | 75 | 52 |
| 11B | 25 | 48 | 38 |

Example 12

Cosmetic Composition

Shampoo

TABLE 15

Shampoo formulation 12.
Data in parts by weight.

| Constituents (INCI name) | Ex. 12 |
|---|---|
| Water | Ad 100 |
| Guar Hydroxypropyltrimonium Chloride[1] | 0.2 |
| Polyquaternium-10[2] | 0.1 |
| Cetearyl Alcohol[3] | 0.5 |
| Glycol Distearate[4] | 1.0 |
| Sodium Laureth Sulfate[5] | 20.0 |
| Cocamidopropyl Betaine[6] | 6.7 |
| Cocamide MEA[7] | 0.5 |
| Carbomer[8] | 0.6 |
| Emulsion from Example 1 | 2.5 |
| Methylchloroisothiazolinone and Methylisothiazolinone[9] | 0.1 |

TABLE 15-continued

Shampoo formulation 12.
Data in parts by weight.

| Constituents (INCI name) | Ex. 12 |
|---|---|
| Triethanolamine[10] | 1.1 |
| Sodium Chloride[11] | 0.3 |

[1] Guar Hydroxypropyltrimonium Chloride: N-Hance ® 3000, Hercules Inc.
[2] Polyquaternium-10: Ucare ™ Polymer JR-400, Amerchol Corporation
[3] Cetearyl Alcohol: Crodacol ® CS50, Croda Chemicals, Europe Ltd.
[4] Glycol Distearate: Genapol ® PMS, Clariant GmbH
[5] Sodium Laureth Sulfate: Genapol ® LRO 26.5%, Clariant GmbH
[6] Cocamidopropyl Betaine: Genagen ® CAB 30%, Clariant GmbH
[7] Cocamide MEA: COMPERLAN ® 100, Cognis Corporation
[8] Carbomer: Carbopol 940 ®, Noveon
[9] Methylchloroisothiazolinone and Methylisothiazolinone: Kathon ™ CG, Rohm and Haas Company, Inc
[10] Triethanolamine: Triethanolamine, Merck KGaA
[11] Sodium Chloride: Sodium Chloride, Merck KGaA Preparation Instructions:

0.2 parts of guar hydroxypropyltrimonium chloride are dispersed in water. With heating to 75° C., 0.1 parts of polyquaternium-10, 0.5 parts of cetearyl alcohol and 1.0 parts of glycol distearate are added. Upon reaching 75° C., 20 parts of sodium laureth sulfate, 6.7 parts of cocamidopropyl betaine and 0.5 parts of cocamide MEA are slowly stirred in. Carbomer is predissolved in some of the water and added. The mixture is then cooled. Upon reaching 50° C., 0.1 parts of methylchloroisothiazolinone and methylisothiazolinone are added. At 35° C., 2.5 parts of the emulsion from example 1 and 0.3 parts of sodium chloride are added. Then, 1.1 parts of triethanolamine are added.

TABLE 16

Shampoo/result of the dry combing force reduction and wet combing force reduction. Improvement in softness. All of the results compared to untreated hair tresses.

| Ex. | Reduction in dry combing force [%] | Reduction in wet combing force [%] | Improvement in softness [%] |
|---|---|---|---|
| 12 | 30 | 18 | 3 |

Example 13

Cosmetic Composition

Hair Mousse

TABLE 17

Hair mousse formulations 13A-13C.
Data in parts by weight.

| Constituents (INCI name) | Ex. 13A | Ex. 13B | Ex. 13C |
|---|---|---|---|
| Water | ad 100 | ad 100 | ad 100 |
| PEG-40 Hydrogenated Castor Oil[1] | 0.5 | 0.5 | 0.5 |
| Aminomethyl Propanol[2] | 1.3 | 1.3 | 1.3 |
| Crotonic Acid/Vinyl C8-12 Isoalkyl Esters/VA/Bis-Vinyldimethicone Crosspolymer[3] | 4.0 | 4.0 | 4.0 |
| Polyquaternium-11[4] | 5.0 | 5.0 | 5.0 |
| Cocamidopropyl Betaine[5] | 5.5 | 5.5 | 5.5 |
| Emulsion from Example 1 | 0.5 | | |
| Emulsion from Example 4 | | 0.2 | |

TABLE 17-continued

Hair mousse formulations 13A-13C.
Data in parts by weight.

| Constituents (INCI name) | Ex. 13A | Ex. 13B | Ex. 13C |
|---|---|---|---|
| Emulsion from Example 5 | | | 0.2 |
| Phenoxyethanol and Methylparaben and Ethylparaben and Butylparaben and Propylparaben and Isobutylparaben[6] | 0.5 | 0.5 | 0.5 |
| Propane/Butane | 8.0 | 8.0 | 8.0 |

[1]PEG-40 Hydrogenated Castor Oil: Cremophor ® RH 40, BASF AG
[2]Aminomethyl Propanol, AMP 30% strength
[3]SLM 28073, Wacker Chemie AG
[4]Polyquaternium-4: Luviquat PQ 11, BASF AG
[5]Cocamidopropyl Betaine: Genagen ® CAB 30%, Clariant GmbH
[6]Phenoxyethanol and Methylparaben and Ethylparaben and Butylparaben and Propylparaben and Isobutylparaben: Phenonip ™, Clariant GmbH Preparation Instructions:

Aminomethyl propanol is dissolved together with PEG-40 hydrogenated castor oil with stirring in water in a beaker. Then with further stirring, the styling polymer crotonic acid/vinyl C8-12 Isoalkyl Esters/VA/Bis-Vinyldimethicone Crosspolymer is added in portions and dissolved.

In a second beaker, water is introduced, and polyquaternium-11, cocamidopropyl betaine and the emulsion according to the examples is added with stirring. Finally, the preservative is added. Then, the solution from beaker 2 is added to the solution from beaker 1 and homogenized. The mixture is poured into cans and supplied with propane/butane as propellent gas mixture.

The hair treated with styling mousse has a pleasant soft feel as a result of using a combination of a silicone copolymer as styling polymer and the dispersion according to the invention of precrosslinked organopolysiloxanes.

TABLE 18

Hair mousse/result of the curl retention after 8 h following treatment with the hair mousse.

| Ex. | Curl retention after 8 h [%] |
|---|---|
| 13A | 28 |
| 13B | 32 |
| 13C | 31 |

The invention claimed is:

1. A method for treating hair, said method comprising applying to the hair a cosmetic composition comprising:
a cosmetically acceptable medium;
at least one hair conditioning agent selected from the group consisting of cationic polymers, cationic surfactants, quaternary ammonium compounds present in nonpolymeric form, organopolysiloxanes, organopolysiloxane copolymers different from precrosslinked organopolysiloxanes of formula (I) below, fatty acid esters, fatty acid alcohols, natural oils, natural waxes, synthetic oils, synthetic waxes, panthenol, lipids, proteins and hydrolyzed proteins, and mixtures thereof; and
at least one aqueous dispersion of precrosslinked organopolysiloxanes of units of the general formula $$AKT_n R_b^2 R_c (OR^1)_d SiO_{\frac{4-(n+b+c+d)}{2}}$$ (I)

where
R is identical or different and is a monovalent, saturated or unsaturated hydrocarbon radical having 1 to 200 carbon atoms per radical, which can contain one or more heteroatoms from the group N, P, S, O, and halogen,
$R^1$ is identical or different and is a hydrogen atom or an alkyl radical having 1 to 8 carbon atoms per radical,
$R^2$ is identical or different and is a monovalent, optionally substituted hydrocarbon radical having 1 to 18 carbon atoms per radical,
AKT is a radical of the formula —$CH_2NHR^4$, —$CH_2NR^4_2$ or

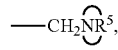

where
$R^4$ is a monovalent hydrocarbon radical having 1 to 18 carbon atoms, which can contain one or more heteroatoms from the group N and O, and
$R^5$ is a divalent hydrocarbon radical having 3 to 12 carbon atoms, which can contain one or more heteroatoms from the group N and O,
b is 0, 1 or 2,
c is 0, 1, 2 or 3,
d is 0, 1 or 2, and
n is 0, 1 or 2,
with the proviso that the sum n+b+c+d is ≤3 and that on average at least one radical AKT is present per molecule.

2. A method for treating hair, said method comprising applying to the hair a cosmetic composition comprising:
a cosmetically acceptable medium;
at least one hair conditioning agent selected from the group consisting of cationic polymers, cationic surfactants, quaternary ammonium compounds present in nonpolymeric form,
organopolysiloxanes, organopolysiloxane copolymers different from precrosslinked organopolysiloxanes of formula (I') below, fatty acid esters, fatty acid alcohols, natural oils, natural waxes, synthetic oils, synthetic waxes, panthenol, lipids, proteins and hydrolyzed proteins, and mixtures thereof; and
at least one aqueous dispersion of precrosslinked organopolysiloxanes of units of the general formula $$AKT_n R_b^2 A_m R'_c (OR^1)_d SiO_{\frac{4-(n+m+b+c+d)}{2}},$$ (I')

where
R' is identical or different and is a monovalent hydrocarbon radical having 1 to 18 carbon atoms,
$R^1$ is identical or different and is a hydrogen atom or an alkyl radical having 1 to 8 carbon atoms per radical,
$R^2$ is identical or different and is a monovalent, optionally substituted hydrocarbon radical having 1 to 18 carbon atoms per radical,
AKT is a radical of the formula —$CH_2NHR^4$, —$CH_2NR^4_2$ or

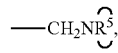

where
$R^4$ is a monovalent hydrocarbon radical having 1 to 18 carbon atoms, which can contain one or more heteroatoms from the group N and O, $R^5$ is a divalent hydrocarbon radical having 3 to 12 carbon atoms, which can contain one or more heteroatoms from the group N and O, A is an amino radical of the general formula

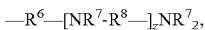
—$R^6$—[$NR^7$-$R^8$—]$_z$$NR^7{}_2$, $R^6$ is a divalent linear or branched hydrocarbon radical having 3 to 18 carbon atoms, $R^7$ is a hydrogen atom, an alkyl radical having 1 to 8 carbon atoms or an acyl radical, $R^8$ is a divalent hydrocarbon radical having 1 to 6 carbon atoms, b is 0, 1 or 2, c is 0, 1, 2 or 3, d is 0, 1 or 2, n is 0, 1 or 2, z is 0, 1, 2, 3 or 4, and m is 0 or 1, with the proviso that the sum n+m+b+c+d is ≤3, and n and m in the same siloxane unit are not simultaneously 1 and that on average at least one radical AKT and a radical A is present per molecule.

3. A method for treating hair, said method comprising applying to the hair a cosmetic composition comprising:
a cosmetically acceptable medium;
at least one hair conditioning agent selected from the group consisting of cationic polymers, cationic surfactants, quaternary ammonium compounds present in nonpolymeric form,
organopolysiloxanes, organopolysiloxane copolymers different from the precrosslinked organopolysiloxane reaction products defined below, fatty acid esters, fatty acid alcohols, natural oils, natural waxes, synthetic oils, synthetic waxes, panthenol, lipids, proteins and hydrolyzed proteins, and mixtures thereof; and
at least one aqueous dispersion of precrosslinked organopolysiloxane reaction products prepared by reacting at least one organopolysiloxane of units of the general formula

$$R_c(OR^1)_d SiO_{\frac{4-(c+d)}{2}} \quad (II)$$

where

R is identical or different and is a monovalent, saturated or unsaturated hydrocarbon radical having 1 to 200 carbon atoms per radical, which can contain one or more heteroatoms from the group N, P, S, O, and halogen, $R^1$ is identical or different and is a hydrogen atom or an alkyl radical having 1 to 8 carbon atoms per radical, c is 0, 1, 2 or 3 and d is 0, 1 or 2, with the proviso that the sum c+d is ≤3 and in the organopolysiloxane on average at least one radical $OR^1$ is present per molecule, with at least one reactive silane of the general formula $(AKT)_a R^2{}_b Si(OR^3)_{4-(a+b)}$ (III) or part hydrolyzates thereof where $R^2$ is identical or different and is a monovalent, optionally substituted hydrocarbon radical having 1 to 18 carbon atoms per radical, $R^3$ is identical or different and is an alkyl radical having 1 to 8 carbon atoms per radical, AKT is a radical of the formula —$CH_2NHR^4$, —$CH_2NR^4{}_2$ or

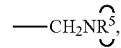
——$CH_2NR^5$, where $R^4$ is a monovalent hydrocarbon radical having 1 to 18 carbon atoms, which can contain one or more heteroatoms from the group N and O, $R^5$ is a divalent hydrocarbon radical having 3 to 12 carbon atoms, which can contain one or more heteroatoms from the group N and O, a is 1 or 2, and b is 0, 1 or 2, with the proviso that the sum a+b is ≤3, in a presence of water, and emulsifier, with the proviso that no metal-containing catalysts are co-used, and that organopolysiloxane and silane are selected in type and amount such that the organopolysiloxanes are precrosslinked in resulting dispersions.

4. The method of claim 3, wherein the precrosslinked organopolysiloxanes produced in this way form elastomeric films after removing the water.

5. The method of claim 3, wherein during the preparation of the aqueous dispersion of precrosslinked organopolysiloxanes, the silane used is at least a trifunctional silane, in which a=1 and b=0.

6. The method of claim 3, wherein during the preparation of the aqueous dispersion of precrosslinked organopolysiloxanes, the radical —$OR^3$ in the silane is an ethoxy radical.

7. The method of claim 3, wherein the radical AKT is a cyclohexylaminomethyl radical or a morpholinomethyl radical.

8. The method of claim 1, wherein the hair conditioning agent is a member selected from the group consisting of:
quaternary ammonium derivative of a cyamopsis tetragonoloba (guar) gum modified with propylene glycol ether,
polymeric quaternary ammonium salt of a reaction product of hydroxyethylcellulose with trimethylammonium-substituted epoxide,
chloride salt of cetyltrimethylammonium, bromide salt of cetyltrimethylammonium, methosulfate salt of cetyltrimethylammonium, chloride salt of behenyltrimethylammonium, bromide salt of behenyltrimethylammonium and methosulfate salt of behenyltrimethylammonium,
N-[3-(dimethylamino)propyl]octadecanamide,
1-octadecanol and 1-hexadecanol,
and mixtures thereof.

9. The method of claim 1, wherein the cosmetically acceptable medium is water.

10. The method of claim 1, wherein the cosmetic composition further comprises cosmetically customary additives selected from the group consisting of surfactants, thickeners, gelling agents, film formers, moisturizing agents, UV filters, pearlizing agents, vitamins, antioxidants, caffeine, antidandruff active ingredients and preservatives.

11. The method of claim 1, wherein the cosmetic composition is prepared by mixing at least one aqueous dispersion of precrosslinked organopolysiloxanes with at least one conditioning agent and optionally further cosmetically customary additives in a cosmetically acceptable medium.

* * * * *